United States Patent [19]

Bucala

[11] Patent Number: 5,733,546
[45] Date of Patent: *Mar. 31, 1998

[54] IMMUNOCHEMICAL DETECTION OF IN VIVO ADVANCED GLYCOSYLATION ENDPRODUCTS

[75] Inventor: Richard J. Bucala, New York, N.Y.

[73] Assignee: The Rockefeller University, New York, N.Y.

[ * ] Notice: The term of this patent shall not extend beyond the expiration date of Pat. No. 5,702,704.

[21] Appl. No.: 484,869

[22] Filed: Jun. 7, 1995

Related U.S. Application Data

[63] Continuation-in-part of Ser. No. 956,849, Oct. 1, 1992, Pat. No. 5,624,804, which is a continuation-in-part of Ser. No. 811,579, Dec. 20, 1991, abandoned.

[51] Int. Cl.$^6$ .................... A61K 39/395; C07K 16/18
[52] U.S. Cl. .................... 424/145.1; 530/388.25; 530/389.3; 530/391.3
[58] Field of Search .................... 530/387.5, 388.2, 530/388.25, 389.1, 389.3, 391.3; 424/145.1

[56] References Cited

U.S. PATENT DOCUMENTS

| | | |
|---|---|---|
| 3,654,090 | 4/1972 | Hermanns et al. . |
| 3,850,752 | 11/1974 | Schuurs et al. . |
| 4,016,043 | 4/1977 | Schuurs et al. . |
| 4,807,973 | 2/1989 | Goers et al. . |
| 5,223,392 | 6/1993 | Cohen . |

FOREIGN PATENT DOCUMENTS

| | | |
|---|---|---|
| WO 89/06798 | 7/1989 | WIPO . |
| WO 93/13421 | 7/1993 | WIPO . |

OTHER PUBLICATIONS

Araki et al. J. Biol. Chem. 267:10211–4 (1992).
Horiuchi, S., et al. J. Biol. Chem. 266 (12):7329–7332 (1991).
Nakayama, H., et al. Biochem. Biophys. Res. Com. 162:740–745 (1989).
Suarez, G., et al. J. Bio. Chem. 264 (7):3674–3679 (1989).
Makita et al. J. Bio. Chem. 267 (8):5133–8 (1992).
Gaulton et al. Ann. Rev. Immunol. 4:253–80 (1986).
Brownlee et al. Annals In. Med. 101:527–37 (1984).
Cohen J. I. Methods 117:121–9 (1989).
Kennedy et al. Diabetologia 26:93–98. (1984).
Vlassara et al., "Functioin of macrophage receptor for nonenzymatically glycosylated proteins is modulated by insulin levels", Diabetes, 35 Supp. 1, p. 13a (1986).
Vlassara et al., "Accumulation of diabetic rat peripheral nerve myeline by macrophages increases with the presence of advanced glycosylation endproducts", A. J. Exp. Med 160, pp. 197–207 (1984).
Vlassara et al., "Recognition and uptake of human diabetic peripheral nerve myelin by macrophages", Diabetes, 34 No. 6, pp. 553–557 (1985).

Vlassara et al., "High–affinity–receptor–mediated uptake and degradation of glucose–modified proteins: a potential mechanism for the removal of senscent macromolecules", Proc. Natl. Acad. Sci. U.S.A., 82, pp. 5588–5592 (Sep. 1985).
Vlassara et al., "Novel macrophage receptor for glucose–modified proteins is distinct from previoiusly described scavenger receptors", J. Exp. Med. 164, pp. 1301–1309 (1986).
Cerami et al., "Role of nonenzymatic glycosylation in atherogenesis", Journal of Cellular Biochemistry, 30, pp. 111–120 (1986).
Radoff, S. et al., "Characterization of a solubilized cell surface binding protein on macrophages specific for proteins modified nonenzymatically by advanced glycosylation end products", Arch. Biochem. Biophys. 263 No. 2, pp. 418–423 (1988).
Yang, Z. et al., "Two novel rat liver membrane proteins that bind advanced glycosylation endproducts: relationship to macrophage receptor for glucose–modified proteins", J. Exp. Med. 174, pp. 515–524 (1991).
Skolnik, E. et al., "Human and rat mesangial cell receptors for glucose–modified proteins: potential role in kidney tissue remodelling and diabetic nephropathy", J. Exp. Med., 174, pp. 931–939 1991.
Makita, Z. et al., "Hemoglobin–age: a circulating marker of advanced glycosylation", Science 258, pp. 651–653 1992.
Horiuchi, S. et al., "Purification of a receptor for formaldehyde–treated serum albumin from rat liver", J. Biol. Chem., 4,260, pp. 482–488 (1985).
Takata, K. et al., "Scavenger receptor–mediated recognition of maleylated albumin and its relation to subsequent endocytic degradation", Biochem. Biophys. Acta., 984, pp. 273–280 (1989).
Goldstein, J.L. et al., "Binding site on macrophages that mediates uptake and degradation of acetylated low density lipoprotein, producing massive cholesterol deposition." Proc. Nat'l Acad. U.S.A. 76, pp. 333–337 (1979).

(List continued on next page.)

*Primary Examiner*—Christina Y. Chan
*Assistant Examiner*—Emma Cech
*Attorney, Agent, or Firm*—Klauber & Jackson

[57] ABSTRACT

The circulating advanced glycosylation endproducts Hb-AGE, serum AGE-peptides and urinary AGE-peptides are disclosed as long term markers of diseases and dysfunctions having as a characteristic the presence of a measurable difference in AGE concentration. Diagnostic and therapeutic protocols taking advantage of the characteristics of these AGEs are disclosed. Antibodies which recognize and bind to in vivo-derived advanced glycosylation endproducts are also disclosed. Methods of using these antibodies as well as pharmaceutical compositions are also disclosed, along with numerous diagnostic applications, including methods for the measurement of the presence and amount of advanced glycosylation endproducts in both plants and animals, including humans, as well as in cultivated and systhesized protein material for therapeutic use.

20 Claims, 12 Drawing Sheets

OTHER PUBLICATIONS

Kirstein, M. et al., "Advanced protein glycosylation induces transendothelial human monocyte chemotaxis and secretion of platelet–derived growth factor: role in vascular disease of diabetes and aging", Proc. Nat'l. Acad. Sci. U.S.A., 87, pp. 9010–9014 (1990).

Flückiger, R. et al., "Measurement of nonenzymatic protein glycosylation", Methods Enzymol., 106, pp. 77–87 (1984).

Bucala, R. et al., "Characterization of Antisera to the Addition Product Formed by the Nonenzymatic Reaction of 16 4Hydrozyestrone with Albumin", Mol. Immunol., 20, pp. 1289–1292 (1983).

Robard, D. "Statistical Quality Control and Routine Data Processing for Radioimmunoassays and Immunoradiometric Assays", Clin. Chem. 20, pp. 1255–1270 (1974).

McPherson et al., "Role of Fructose in Glycatioin and Cross–Linking of Proteins", Biochemistry, 27, pp. 1901–1907 (1988).

Radoff, S. et al., "Isolation of a Surface Binding Protein Specific for Advanced Glycosylation Endproducts from the Murine Macrophage–Derived Cell Line Raw 264.7", Diabetes, 39, pp. 1510–1518 (1990).

Mitchel, F. et al., "Darstellung Aliphatischer Amadori–Produkte", Chem Ber., 92, pp. 2836–2840 (1959).

Bradford, M., "A Rapid and Sensitive Method for the Quantitation of Microgram Quantities of Protein Utilizing the Principle of Protein–Dye Binding", Anal. Biochem., 72, pp. 248–252 (1976).

Edward, C. et al., "Modified Assay for Determination of hydroxyproline in a Tissue Hydrolyzate", Clin. Clim. Acta., 104, pp. 161–167 (1980).

Radoff et al. (1991) Diabetes 40:1731–8.

Bucala et al. (1993) Proc. Natl. Acad. Sci. U.S.A., 90:6434–8.

Nakayama et al. (1991) J. Immunol. Methods 140:119–25.

Chang et al. (1985) J. Biol. Chem. 260:7970–4.

Atuned et al. (1992) Clin. Chem. 38/7:1301–3.

Njoroge et al. (1988) J. Biol. Chem. 263:10646–52.

Lapolla et al. (1990) Diabetes 39:1990.

Miyata et al. (1993) J. Clin. Invest. 92:1243–52.

Horiuchi et al. (1993) Progress in Diabetology:238–43 (English Abstract).

Horiuchi et al. ($\leq$1993) p. 186 (English Abstract).

Harlow et al. Antibodies a Laboratory Manual, Cold Spring Harbor Laboratory, Cold Spring Harbor, 1984.

IMMUNOCHEMICAL DETECTION OF IN VIVO ADVANCED GLYCOSYLATION ENDPRODUCTS

CROSS-REFERENCE TO RELATED APPLICATION

The present Application is a a Continuation-In-Part of application Ser. No. 07/956,849, filed Oct. 1, 1992, now U.S. Pat. No. 5,624,804, which is a Continuation-In-Part of application Ser. No. 07/811,579, filed Dec. 20, 1991, now abandoned, by the inventor herein. Priority under 35 U.S.C. §120 is claimed as to the above earlier filed Applications, and the disclosures thereof are incorporated herein by reference in their entireties.

RELATED PUBLICATIONS

The following articles are noted as they are generally directed to the subject matter of the present invention: "FUNCTION OF MACROPHAGE RECEPTOR FOR NONENZYMATICALLY GLYCOSYLATED PROTEINS IS MODULATED BY INSULIN LEVELS", Vlassara, Brownlee and Cerami, DIABETES (1986), Vol. 35 Supp. 1, Page 13a; "ACCUMULATION OF DIABETIC RAT PERIPHERAL NERVE MYELIN BY MACROPHAGES INCREASES WITH THE PRESENCE OF ADVANCED GLYCOSYLATION ENDPRODUCTS", Vlassara, H., Brownlee, M., and Cerami, A. J. EXP. MED. (1984), Vol. 160, pp. 197–207; "RECOGNITION AND UPTAKE OF HUMAN DIABETIC PERIPHERAL NERVE MYELIN BY MACROPHAGES", Vlassara, H., Brownlee, M., and Cerami, A. DIABETES (1985), Vol. 34, No. 6, pp. 553–557; "HIGH-AFFINITY-RECEPTOR-MEDIATED UPTAKE AND DEGRADATION OF GLUCOSE-MODIFIED PROTEINS: A POTENTIAL MECHANISM FOR THE REMOVAL OF SENESCENT MACROMOLECULES" Vlassara H., Brownlee, M., and Cerami, A., PROC. NATL. ACAD. SCI. U.S.A. (Sept. 1985), Vol. 82, pp. 5588–5592; "NOVEL MACROPHAGE RECEPTOR FOR GLUCOSE-MODIFIED PROTEINS IS DISTINCT FROM PREVIOUSLY DESCRIBED SCAVENGER RECEPTORS" Vlassara, H., Brownlee, M., and Cerami, A. JOUR. EXP. MED. (1986), Vol. 164, pp. 1301–1309; "ROLE OF NONENZYMATIC GLYCOSYLATION IN ATHEROGENESIS", Cerami, A., Vlassara, H., and Brownlee, M., JOURNAL OF CELLULAR BIOCHEMISTRY (1986), Vol. 30, pp. 111–120; "CHARACTERIZATION OF A SOLUBILIZED CELL SURFACE BINDING PROTEIN ON MACROPHAGES SPECIFIC FOR PROTEINS MODIFIED NONENZYMATICALLY BY ADVANCED GLYCOSYLATION END PRODUCTS", Radoff, S., Vlassara, H. and Cerami, A., ARCH. BIOCHEM. BIOPHYS. (1988), Vol. 263, No. 2, pp. 418–423; "ISOLATION OF A SURFACE BINDING PROTEIN SPECIFIC FOR ADVANCED GLYCOSYLATION ENDPRODUCTS FROM THE MURINE MACROPHAGE-DERIVED CELL LINE RAW 264.7", Radoff, So, Vlassara, H., and Cerami, A., DIABETES, (1990), Vol. 39, pp. 1510–1518; "TWO NOVEL RAT LIVER MEMBRANE PROTEINS THAT BIND ADVANCED GLYCOSYLATION ENDPRODUCTS: RELATIONSHIP TO MACROPHAGE RECEPTOR FOR GLUCOSE-MODIFIED PROTEINS", Yang, Z., Makita, Z., Horii, Y., Brunelle, S., Cerami, A., Sehajpal, P., Suthanthiran, M. and Vlassara, H., J. EXP. MED., Vol. 174, pp. 515–524; "HUMAN AND RAT MESANGIAL CELL RECEPTORS FOR GLUCOSE-MODIFIED PROTEINS: POTENTIAL ROLE IN KIDNEY TISSUE REMODELLING AND DIABETIC NEPHROPATHY", Skolnik, E., Yang, Z., Makita, Z., Radoff, S., Kirstein, M., and Vlassara, H., J. EXP. MED., Vol. 174, pp. 931–939; and "HEMOGLOBIN-AGE: A CIRCULATING MARKER OF ADVANCED GLYCOSYLATION", Makita, Z., Vlassara, H., Rayfield, E., Cartwright, K., Friedman, E., Rodby, R., Cerami, A., and Bucala, R., SCIENCE, (In Press). All of the foregoing publications and all other references cited herein are incorporated by reference.

BACKGROUND OF THE INVENTION

The present invention relates generally to the detection and measurement of nonenzymatically glycosylated proteins, and particularly to methods and associated materials for the detection and measurement of proteins that have been nonenzymatically glycosylated in vivo.

Reducing sugars, e.g., glucose, have been shown to react non-enzymatically with protein amino groups to form a diverse series of protein bound moieties with fluorescent and crosslinking properties. These compounds, called advanced glycosylation endproducts ("AGEs"), have been implicated in the structural and functional alteration of proteins during aging and in certain diseases, e.g., long-term diabetes. Several AGEs have been identified on the basis of de novo synthesis and tissue isolation procedures.

The reaction between reducing sugars and the free amino groups of proteins initiates the post-translational modification process called advanced glycosylation. This process begins with a reversible reaction between the reducing sugar and the amino group to form a Schiff base, which proceeds to form a covalently-bonded Amadori rearrangement product. Once formed, the Amadori product undergoes further rearrangement to produce AGEs.

Because these reactions occur slowly, proteins may accumulate significant amounts of Amadori products before accumulating a measurable amount of AGEs in vivo. These AGEs can cause protein crosslinking, which in turn may reduce the structural and/or functional integrity of organs and organ parts, thus ultimately reducing or impairing organ function.

The advanced glycosylation process is particularly noteworthy in that it occurs in proteins with long half-lives, such as collagen and under conditions of relatively high sugar concentration, such as in diabetes mellitus. Numerous studies have suggested that AGEs play an important role in the structural and functional alteration which occurs in proteins during aging and in chronic disease.

Additionally, advanced glycosylation endproducts are noted to form more rapidly in diabetic, galactosemic and other diseased tissue than in normal tissue.

Certain advanced glycosylation endproducts are believed to have in common a characteristic yellow-brown pigmentation, a characteristic fluorescence spectrum and the ability to form protein-protein crosslinks. AGEs form in vivo and have been isolated from naturally glycosylated material. These products are present in low abundance, are structurally heterogeneous and are labile to chemical reduction and hydrolysis. De novo synthesis and isolation procedures have led to the identification of several AGEs, such as 2-(2-furoyl)-4(5)-(2-furanyl)-1H-imidazole ("FFI"); 5-hydroxymethyl-1-alkylpyrrole-2-carbaldehyde ("Pyrraline"); 1-alkyl-2-formyl-3,4-diglycosyl pyrrole ("AFGP"), a non-fluorescent model AGE; carboxymethyllysine; and pentosidine. However, the in vivo formation of AGEs is not limited to these precise chemical compounds, and newly discovered AGEs are addressed herein.

The study of specific AGEs synthesized in vitro in the past has necessitated the use of chemical reduction and hydrolysis procedures. This has left open the possibility that naturally occurring AGEs would include other compounds with alternative structures which differ from the model compounds which have been isolated.

Efforts have also been made to develop antibodies to in vivo AGEs, however no instances of success are known or have been reported. Thus, Nakayama et al., BIOCHEM. BIOPHYS. RES. COMM., 162:2, pp. 740–745 (1989) studied protein bound AGEs and in particular, raised antisera against AGE-KLH derived from in vitro glycosylation. These antisera exhibited high affinity binding, and the serial dilution curves of in vitro-formed AGE-BSA, AGE-HSA and AGE-RNAse A were noted to parallel each other, suggesting that a structure in common among these particular AGE-proteins is recognized by the antisera. Further study to determine whether the structure recognized stems from advanced Maillard reactions or from the early-stage compounds, such as Schiff base adducts and Amadori rearrangement products were conducted using a number of reducing agents. Treatment with a reducing agent did not decrease immunoreactivity, and FFI was not recognized by the antibodies. Importantly, the antibodies prepared and tested by Nakayama et al. were not determined to react with AGEs formed in vivo.

Horiuchi et al., J. BIOL. CHEM., 266(12), pp. 7329–7332 (1991) prepared polyclonal and monoclonal antibodies against in vitro-derived AGE-bovine serum albumin. The Horiuchi et al. antibodies also recognized in vitro-derived AGE-human serum albumin and AGE-hemoglobin, but did not recognize unmodified counterparts. Treatment of these AGE proteins with a reducing agent had no effect on immunoreactivity. Like the antibodies of Nakayama et al., the antibodies prepared by Horiuchi et al. were not determined to react with in vivo-formed AGEs.

Accordingly, despite the facility with which antibodies have been prepared in the art, the reactivity of such antibodies with in vivo-formed AGEs has not been previously achieved. The preparation of such antibodies is desirable as it makes possible the development and implementation of diagnostic and therapeutic protocols addressing the formation of advanced glycosylation endproducts in mammals including humans.

In this context, parent Application Serial No. 07/811,579, now abandoned discloses the preparation of an antiserum that contains antibodies reactive with in vivo-formed advanced glycosylation endproducts. Among the advanced glycosylation endproducts against which antibodies were raised, the reaction product of hemoglobin and a reducing sugar (Hb-AGE) was included. In addition, data were presented that compared this AGE favorably with $HbA_{1c}$ in terms of its use as a diagnostic agent.

The present application seeks to present further data cumulative on the activity of Hb-AGE, thereby emphasizing its expanded capabilities. Also, the role of serum- and urinary AGE peptides as markers of disease and dysfunction is further elaborated herein.

SUMMARY OF THE INVENTION

In a first aspect of the present invention, the advanced glycosylation endproduct involving a complex with hemoglobin, referred to hereinafter as Hb-AGE, is reviewed in further detail and particularly with regard to its capability as a diagnostic tool. Accordingly, Hb-AGE exhibits a broad range of activity, in that Hb-AGE and/or its antibodies may be used not only in detecting the onset of either glycemic conditions or diabetes mellitus, but also in the long term monitoring of the course of such conditions, to detect fluctuations in the intensity of such conditions. Likewise, therapeutic applications for both Hb-AGE and its antagonists are contemplated.

The present invention also extends to the measurement of urinary- and serum AGE-peptides and to the diagnostic and therapeutic applications that follow. Urinary AGE-peptide levels are indicative of the turnover of tissue AGEs and are therefore also useful in the evaluation of diabetes and diabetic complications, and particularly, the control of blood glucose levels, both short term and long term, e.g., up to about 60–90 days. Serum AGE-peptides are predictive of renal disease, and particularly may be measured to determine glomerular filtration rate (GFR). Accordingly, diabetic complications involving the kidney can be monitored and serum AGE-peptides can be used to evaluate the effect of test compounds on the kidney and the level of AGEs elsewhere in the body. Serum peptide-AGEs are also useful for detecting the AGE-inducing or -forming effect of drugs, and in evaluating the therapeutic effect of AGE inhibitors, since serum peptides are derived from long-lived proteins.

Accordingly, the present invention relates to the measurement of Hb-AGE, serum AGE-peptides and urinary AGE-peptides, and to the associated methods for both the long-term and short-term monitoring of conditions involving either sugar concentrations or AGE concentrations. The invention also includes the measurement of mammalian and particularly human serum albumin AGEs (AGE-HSA), as well as food products for the assessment of spoilage, and proteins including recombinant preparations, that are intended for use as therapeutic agents. In this last mentioned connection, the invention includes the use of the present AGE antibodies in a method for monitoring the purity of such protein preparations, and a related method for the purification of the preparations that remove glycosylated proteins therefrom. Such a method would limit the unwanted administration of glycosylated proteins that are known to be clinically active in a manner deleterious to the host.

The method of assessing the presence or activity of disease in which Hb-AGE is the marker comprises obtaining a blood or other serum sample from a mammal, determining the presence or amount of Hb-AGE in the sample and comparing this amount to a standard.

Hb-AGE measurements provide an appropriate index of long-term tissue modification by AGEs and are useful in assessing the contribution of advanced glycosylation to a variety of diabetic and age-related complications. While hemoglobin $A_{1c}$ ($HbA_{1c}$) has been reported as predictive of the extent of glycation on the hemoglobin β chain, $HbA_{1c}$ is only an intermediate in the advanced glycosylation pathway and numerous other intermediates are believed to exist. Moreover, $HbA_{1c}$ is not predictive of pathology. Therefore, Hb-AGEs levels are believed to be a better measure of disease, drug effectiveness, etc. Hb-AGEs are used in the present invention to more readily correlate to the progression of disease and longer term control of blood sugar levels, which is greater than about 3–4 weeks. The reduction in Hb-AGE levels as a result of aminoguanidine therapy is a primary example of the detection of successful pharmacological inhibition of advanced glycosylation in human subjects.

The invention also extends to the embodiment thereof that is common to the present disclosure and that of parent application Serial No. 07/811,579, now abandoned, concerning antibodies which react with in vivo-produced advanced glycosylation endproducts. Included therefore, is an antiserum that contains antibodies reactive with in vivo-formed advanced glycosylation endproducts and has the following characteristics:

A. it reacts with an immunological epitope common to in vivo-formed advanced glycosylation endproducts;

B. it is cross reactive with advanced glycosylation endproducts formed in vitro; and C. it is not cross reactive with the following advanced glycosylation endproducts however formed: FFI, AFGP, pyrraline, and pentosidine. Particularly, the common epitope is formed by the incubation of a reducing sugar with a proteinaceous material selected from the group consisting of RNAse, lysine, hemoglobin, collagen Type IV, LDL, BSA and HSA.

The present application further reconsiders the reactivity of the antibodies of the invention with the AGE carboxymethyllysine. Although the data presented herein indicate low, if any, reactivity of the antibodies with this AGE, subsequent evaluations with antibodies of the invention suggest some recognition of this AGE. Accordingly, the present application relates to detection of AGEs including carboxymethyllysine, a characteristic that is inherent to the antibodies of the invention as disclosed herein.

The antibodies of the invention may be polyclonal or monoclonal, and if the latter, may be prepared by the hybridoma method, or other known recombinant techniques. As illustrated herein, the antibodies may be raised in an immunocompetent mammal by hyperimmunizing said mammal with AGEs or a protein on which AGEs have been formed. The antibodies produced recognize and bind to in vivo-formed AGEs, samples which contain such AGEs, e.g., diabetic tissue or serum, as well as in vitro-formed AGEs which form on proteins as a result of incubation with sugars.

The anti-AGE antibodies of the invention are likewise characterized in that they do not recognize certain AGEs that have been synthetically produced, e.g., FFI, pyraline, AFGP, and pentosidine.

The anti-AGE antibodies described herein are further characterized as follows:

(a) the antibodies can be formed by hyperimmunization of a mammal with AGE-RNAse;

(b) the antibodies are reactive with the following AGEs: AGE-RNAse, AGE-hemoglobin, AGE-BSA, AGE-HSA, AGE-collagen IV, AGE-LDL and AGE-lysine;

(c) the antibodies are non-reactive with unmodified HSA or BSA, FFI-BSA, formylated-albumin, maleylated-albumin, LDL, collagen IV, acetyl-LDL, FFI, AGFP, pyrraline, pentosidine, lysine, deoxypropylaminofructose or deoxymorpholinofructose.

In a further aspect of the invention, the present anti-AGE antibodies may be recovered from an antiserum raised in a suitable host which has been inoculated with a particular AGE-protein. The preferred method comprises administering to an immunocompetent mammal an effective amount of an AGE or a compound containing AGEs as above described, to induce the formation of the present anti-AGE antibodies, and obtaining from the mammal a serum which contains the anti-AGE antibodies. A particular AGE-protein comprises the product of the incubation of RNAse with glucose.

Another aspect of the present invention relates to immunological assays for detecting the presence or quantity of AGEs in a sample, comprised of:

(a) binding a sample suspected of containing AGEs, an AGE carrier, anti-AGE antibodies or another AGE binding partner to a solid support;

(b) contacting the specie attached to the solid support with an analyte to be tested for the presence or quantity of AGEs, anti-AGE antibodies or other AGE binding partner;

(c) labelling the AGEs, anti-AGE antibodies or other binding partner with a detectible label; and (d) comparing the amount of bound label to a standard.

The above assay format may be adapted to examine samples of plant and animal matter for the presence of AGEs, for example to detect the likelihood or onset of food spoilage, and the present invention is intended to extend to this utility.

The invention further encompasses the use of the present antibodies for the detection of disease in a mammal, which is characterized in that an abnormal level of AGEs such as Hb-AGE, serum AGE peptides and urinary AGE peptides, is present. The antibodies may be either polyclonal or monoclonal, and are as characterized earlier herein.

Assay kits are also encompassed which are useful for performing the assay/diagnosis described herein, which include suitable reagents for detecting or quantifying AGEs such as Hb-AGE, urinary- and serum AGE-peptides, AGE-antibodies or other AGE binding partners in a sample.

Therapeutic compositions and methods of use in the prevention, diagnosis or treatment of disease using these compositions are also included, wherein an effective amount of the composition is administered to a patient in need of such treatment.

Consequently, a primary object of the present invention is to provide an antiserum which contains antibodies which recognize and bind to in vivo-formed AGEs, and a method of making the antiserum containing anti-AGE antibodies which have not heretofore been produced.

Another object of the invention described herein is to provide immunochemical assay protocols using the antiserum described above, for proteins which are modified by advanced glycosylation. AGE-immunogens have been prepared in vitro without the use of chemical reduction and hydrolysis procedures, and antisera have been produced in vivo using these AGEs.

Another object of the present invention is to provide immunoassay protocols which encompass the use of polyclonal antibodies raised in response to an immunogenic challenge with AGEs, as well as monoclonal antibodies all of which are specific to in vivo AGE epitopes.

It is a further object of the present invention to provide a method for measuring advanced glycosylation endproducts in a variety of biological samples that is rapid and reliable, taking advantage of the anti-AGE antibodies which have been raised and characterized.

It is a further object of the present invention to provide kits containing suitable reagents for the measurement of AGEs including as the internal standard a material selected from Hb-AGE, serum AGE-peptides and urinary AGE-peptides, which are suited to a broad range of alternative immunological protocols.

It is a still further object of the present invention to provide a method for the long term monitoring of glycemic conditions including diabetes, by the measurement of AGEs such as Hbo-AGE, serum AGE-peptides and urinary AGE-peptides, that is fast and reliable.

These and other objects will be apparent to the ordinarily skilled artisan from a review of the detailed description taken in conjunction with the following drawings.

BRIEF DESCRIPTION OF THE DRAWINGS

(FIG. 2A): Reaction with a variety of modified albumins. Glucose-derived AGE-BSA (●), G6P-derived AGE-BSA (▲), Fructose-derived AGE-BSA (▼), FFI-BSA (Δ), Formylated-BSA (▽), Maleyl-BSA (◊), and BSA (○).

(FIG. 2B): Reaction with AGE-modified and unmodified proteins. G6P-derived AGE-HSA (●), Glucose-derived AGE-LDL (▲), Glucose-derived AGE-collagen IV (♦), Glucose-derived AGE-RNAse (■), HSA (○), LDL (Δ), acetyl-LDL (▽), collagen IV (◊), RNAse (□). LDL nmoles were calculated on the basis of the molecular weight of apoprotein B.

(FIG. 2C): Reaction with model AGEs. Glucose-derived AGE-lysine (●), G6P-derived AGE-lysine (♦), FFI-HA (○), pyrraline (▲), AFGP (▼), carboxymethyllysine (■), pentosidine (□), deoxypropylaminofructose (Δ), and deoxymorpholinofructose (▽). AGE-lysine products were added as nmoles of lysine equivalents;

(FIG. 5A): Relative fluorescence measured at $\lambda_{excitation}$370 nm and $\lambda_{emission}$440 nm). (FIG. 5B): Collagen-bound AGEs measured by ELISA. Control rats (○), rats with alloxan-induced diabetes (▲), and rats with streptozotocin-induced diabetes (▼). Each value shown is the mean of six experimental animals;

DETAILED DESCRIPTION OF THE INVENTION

Figure 1:
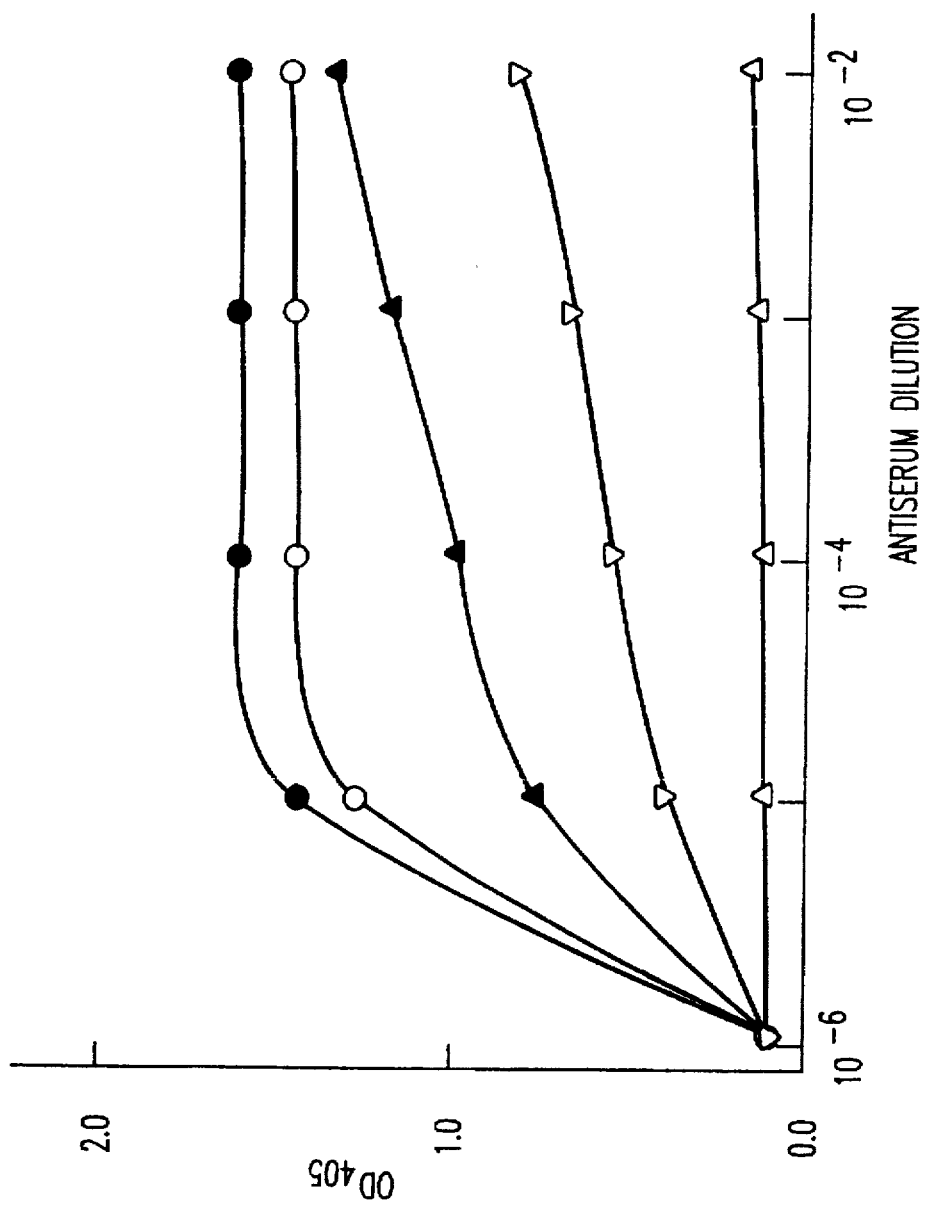
FIG. 1 is an antiserum dilution curve for anti-AGE-RNAse antiserum. Antiserum was titered in a noncompetitive ELISA utilizing the following absorbed antigens: RNAse (○), Glucose-derived AGE-RNAse (●), BSA (Δ), Glucose-derived AGE-BSA (▲), and G6P-derived AGE-BSA (▼)

Numerous abbreviations are used herein to simplify the terminology used, and to facilitate a better understanding of the invention. The following abbreviations are representative.

As used herein, the terms "AGE" and "AGEs" are used as appropriate to refer to advanced glycosylation endproducts which are in the form of intermediates and stable compounds which are produced in vivo and in vitro by the reaction of reducing sugars with protein amino groups. AGEs therefore encompass intermediates as well as stable endproducts that are implicated in the structural and functional alteration of proteins seen during aging. For example, AGEs are recognized to react with free polypeptide amino groups, which leads to protein crosslinking. Additionally, such AGEs are observed in elevated levels in circulation and in tissues in certain diseases, e.g. diabetes mellitus.

When the designations "AGE-RNAse", "AGE-Hb", "AGE-BSA", "AGE-HSA", "AGE-albumin", "AGE-collagen" and "AGE-LDL" are used, each refers to the advanced glycosylation endproducts which are formed upon chemical reaction of the substrates RNAse, Hb, BSA, HSA, albumin, collagen and LDL, respectively with one or more reducing sugars. Thus, AGE-RNAse refers to the advanced glycosylation endproducts of the reaction between bovine ribonuclease and a reducing sugar.

Albumin, when recited generically, refers to any specie from which it was obtained, e.g., human, bovine, etc.

BSA refers to bovine serum albumin.

HSA refers to human serum albumin.

RNAse refers to ribonuclease generally, and where appropriate, to bovine pancreatic ribonuclease in particular.

Collagen is used in the conventional sense to refer to any type of collagen and derived from any appropriate source. When a specific type of collagen was used, such as in the example, the particular type is noted. However, it is recognized that alternative collagen types can also be used.

LDL is also used in the conventional sense to refer to low density lipoprotein.

FFI-BSA refers to a model AGE-protein produced by incubating 2-(2-furoyl)-4(5)-(2-furanyl)-1H-imidazole hexanoic acid with bovine serum albumin and coupling the reactive compounds with dicyclohexylcarbodiimide. Formaldehyde-BSA, maleyl-BSA and acetyl-LDL all refer to modified proteins produced as described below.

The present invention relates to the measurement of certain in vivo-generated AGEs and particularly Hb-AGE, serum AGE peptides and urinary AGE peptides, and to the diagnostic and therapeutic applications to which such measurement may be put. The use of Hb-AGE as a marker facilitates the long-term measurement of blood sugar levels and the consequent ability to monitor glycemic conditions such as exist in diabetes mellitus. As the data presented herein reveals, Hb-AGE in contrast to the known determinant $HbA_{1c}$, decreases in response to the administration of the in vivo glycation inhibitor aminoguanidine and thus represents a clinically accurate time-integrated parameter of recent blood sugar levels that possesses the added dimension of use for both diagnostic and therapeutic purposes.

Figure 9:
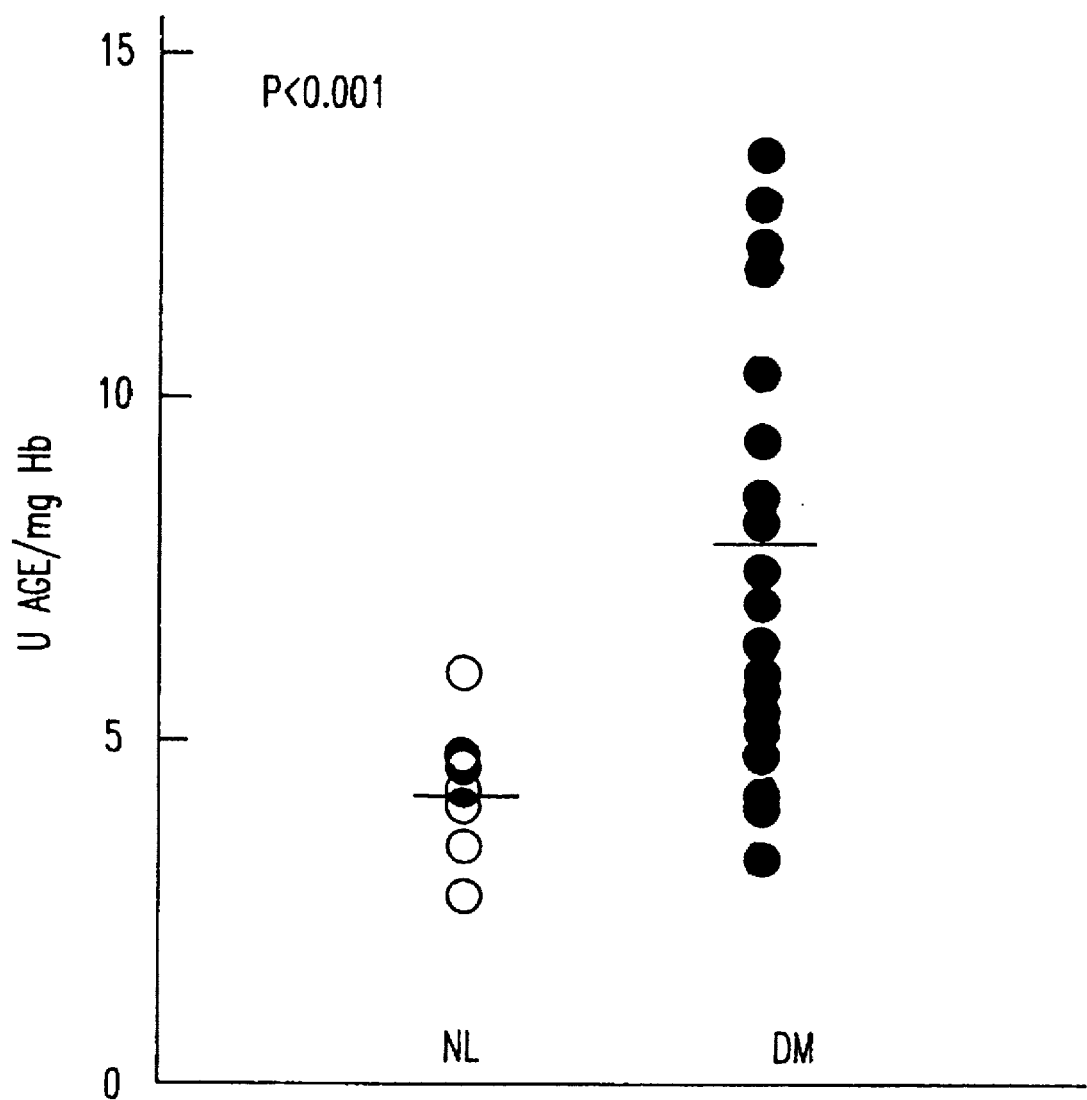
FIG. 9 is a graph depicting the results of the ELISA of Hb-AGE levels measured in 23 diabetic individuals (DM) and 9 non-diabetic, normoglycemic individuals (NL). NL: 4.3±0.3 AGE Units/mg Hb, DM: 7.7±0.6 AGE Units/mg Hb, (Mean±S.E.). Each value represents the mean of triplicate determinations, assayed at 3–4 hemoglobin dilutions to ensure that measured values fell within the linear range of the ELISA standard curve. AGE units are calculated relative to an AGE-albumin standard synthesized and analyzed for AGE content as described.
Figure 10:
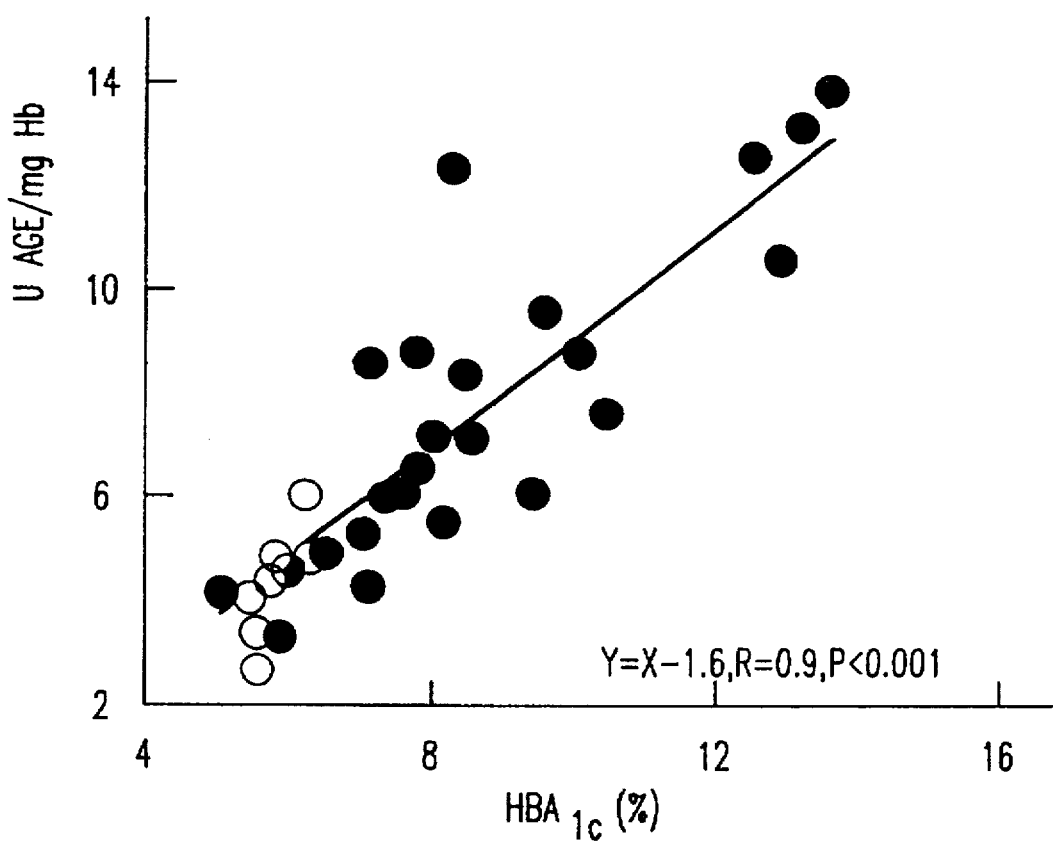
FIG. 10 graphically shows a correlation between levels of Hb-AGE and $HbA_{1c}$ for nine normoglycemic (○) and 23 diabetic (●) individuals. $HbA_{1c}$ was measured by HPLC.

Particularly, the present invention takes advantage of a competitive ELISA developed with the anti-AGE antibodies that form a part hereof and that are also comprehensively presented in parent application Serial No. 07/811,579, now abandoned, and comprises a quick and effective diagnostic method. As shown in FIG. 9, Hb-AGE represents a stable and reliable glucose-derived rearranged Amadori product around which a diagnostic protocol may be developed and carried out. Accordingly, the invention extends to a method for the long term monitoring of in vivo glycemic conditions and the concomitant assessment of the efficacy of any control measures that may be implemented.

The present invention also extends to the measurement of other AGEs and particularly serum and urinary AGE-peptides. Serum and urinary AGE-peptides, like Hb-AGE, represent circulating markers of AGE accumulation that reflect the onset and extent of pathologies and other dysfunctions where such accumulation is a characteristic. Thus, those age-related and diabetic conditions where increased levels of AGEs have been observed, such as, for example, atherosclerosis, cataracts and diabetic nephropathy, may be monitored and assessed over the long term by the measurement of these AGEs, particularly by resort to the diagnostic methods disclosed herein.

Likewise, the methods including Hb-AGE or the noted AGE-peptides as markers or determinants may be used as a drug discovery assay, for identification of drugs or other modalities that may interact with these AGEs. In the instance of Hb-AGE, it may be possible to discover agents that may control either the concentration of blood glucose or the formation of Hb-AGE itself. An assay or test kit in such instance would include the reagents set forth for such kits presented later on herein, with Hb-AGE as the ligand or binding partner. A similar assay or kit may be prepared with the noted AGE peptides serving in like capacity to Hb-AGE.

The investigation of AGE formation in vivo has been hampered by a lack of specific assay methods and by the general inaccessibility of tissue AGEs to in vivo analysis. The realization that Amadori products such as $HbA_{1c}$ are AGE precursors led to a consideration that hemoglobin might also acquire AGE modifications that could be measured with recently developed ELISA techniques.

Hb-AGE has been determined to account for about 0.42% of circulating human hemoglobin. This fraction increases to approximately 0.75% in patients with diabetes-induced hyperglycemia. Of significance, diabetic patients treated for 28 days with aminoguanidine, an inhibitor of AGE formation in vivo, showed significantly decreased levels of Hb-AGE at the end of the treatment period.

The tissue and end organ damage caused by advanced glycosylation accumulates over a period of months to years. Diabetic complications progress over a similar duration.

As stated above, a particularly preferred aspect of the present invention is the use of Hb-AGE as an indicator of the extent of control of blood glucose in diabetes patients. Taking into account the normal Hb-AGE levels and the reaction time over which Hb-AGE is formed, the level of Hb-AGE present in the blood can be predictive of diseases and underlying pathology where the level of Hb-AGE is above normal values.

Similarly, serum peptide-AGEs can be used as an indicator that reflects glomerular filtration rate (GFR) and kidney damage. Urinary AGE-peptides may be used as an indicator to measure the turnover in tissue proteins, and more particularly, tissue-AGE proteins.

In both the Hb-AGE and the serum AGE-peptide assays, the blood sample is drawn and a separation procedure can be used. The cellular blood components can be separated from the serum, and in the Hb-AGE assay, the hemoglobin can be extracted from the red blood cells. The serum level of AGE-peptides and the presence or extent of Hb-AGEs present can then be evaluated.

By conducting both tests with a single blood sample, a broader time frame at which blood glucose levels become uncontrolled can be estimated, e.g., a 60 day range predictable by Hb-AGE that extends to the periods before, during or after the 3–4 week time frame which is predicted by $Hb-A_{1c}$. If desired, the analyses of Hb-AGE and serum AGE-peptides can also be run together with a glucose level determination in blood or urine, a glucose tolerance test, and other tests useful for assessing diabetes control including the measurement of urinary AGE-peptides, to give a complete patient profile.

Another aspect of the invention addresses advanced glycosylation endproducts which can be detected in the urine. Proteins, including peptides, are excreted in the urine in low levels in normal individuals, and in perhaps elevated levels in diseased individuals. The presence and/or level of urinary AGE-peptides reflective of the turnover of tissue AGEs can be determined, correlated to and predictive of particular diseases or conditions. For example, the quantity of peptides found in normal urine usually ranges from about 25 to 50 mg per day and is comprised of microproteins, with properties which are quite different from the predominant blood proteins, albumin and globulin.

The presence of proteins in the urine may be a symptom of numerous diseases or conditions reflective of a net catabolic state as would exist when the host or patient is undergoing invasion as by infection. Under such circumstances, the host mobilizes against the invasive stimulus by the secretion of numerous factors such as cytokines that suspend the anabolic energy storage activity and cellular repair activities and promote instead the catabolic depletion of energy stores and the recruitment of leukocytes and other factors to fight and neutralize the stimulus. As this activity results in a corresponding elevation in tissue protein levels, and corresponding levels of tissue-AGEs, the measurement of urinary AGE-peptides provides yet another index of possible invasive activity in the host, such as cachexia and shock. Thus, one can measure the presence or level of AGE-peptides in urine, and correlate this level to a standard. In normal individuals, the normal level may be at or close to zero. In diabetic patients or in patients experiencing infection or other trauma, the normal level of AGE-peptides may be significantly greater. Thus, the advancement or worsening of diabetes prior to the onset of renal complications, or the presence of infection could be detected by detecting increases in urine levels of AGE-peptide.

Likewise, one may be able to detect individuals who glycosylate proteins faster than normal. In this instance, one would determine the level of AGE-peptides in the urine as a result of a specific challenge, e.g., with glucose, a compound which induces AGE formation or release by the proteins of the body, or the rate at which urinary peptide-AGE levels increase after cessation of the administration of an AGE inhibiting compound, e.g., aminoguanidine. A full clinical picture will therefore become apparent.

The present invention also relates to detecting the presence or level of such AGE-peptides in serum. This may take into account the extent of AGE accumulation and reaction with extracellular and cellular blood proteins, protein fragments and peptides (shorter chain amino acids, e.g., up to about 50 amino acids in length) found in the circulatory system. These can be evaluated for the presences or level of AGEs, the extent of advanced glycation determined, and compared to a standard, e.g., normal peptide glycation levels. For example, if one detects an elevated level of AGE-peptides in the blood, one may correlate this to the extent of kidney damage sustained by the patient.

Amadori products are slowly reversible and are believed to attain equilibrium over a 3–4 week period. AGEs, in contrast, remain irreversibly attached to proteins and continue to accumulate over the lifespan of the protein. The utility of Hb-AGE measurements as a long term in vivo marker of advanced glycosylation can thereby be appreciated.

As stated earlier, the invention also comprises the identification of an antiserum and corresponding antibodies that recognize and bind to in vivo-formed advanced glycosylation endproducts. As demonstrated in the examples presented later on herein, polyclonal AGE-ribonuclease antiserum has been prepared and used in competitive ELISA systems to study the specificity of this antiserum for in vitro- and in vivo-derived products. The resulting antiserum recognized and bound to in vivo AGEs in diabetic tissue and serum known to contain abnormally elevated levels of AGEs, leading to the conclusion that a common epitope exists among them. By contrast, each of the model, synthetic AGEs which were synthesized and tested failed to react with the polyclonal antiserum, although other in vitro-formed AGEs are reactive.

Examples of proteins and protein-containing substances suitable for incubation-type reactions with the reducing sugars include, for example, RNAse, hemoglobin, collagen, BSA and HSA, each of which can be incubated with, e.g., glucose, glucose-6-phosphate ("G6P"), fructose or ribose to produce a suitable AGE immunogen for inducing the formation of anti-AGE antibodies.

Such anti-AGE antibodies can also be used in the treatment of patients to reduce the level of circulating AGEs or AGEs which may be present in abnormally elevated levels in certain tissues, e.g., pancreas, liver, kidney or brain.

Additionally, it is within the scope of the invention described herein to utilize the anti-AGE antibodies for the design, screening and/or potentiation of drugs or compounds which are useful for treating elevated levels of AGEs in vivo. In this connection, the anti-AGE antibodies may be used to purify proteins that have been specially cultivated or produced for use as therapeutic agents. As stated earlier, the therapeutic use of such proteins is increasing in prominence and importance, and such proteins like other host cells, are susceptible to glycation and the formation of AGEs. As such AGEs are particularly clinically active, it is desirable to limit their introduction into a host during therapy. As a consequence, the present invention includes a method for purification of batches of such proteins by bringing them into contact with, for example, a quantity of anti-AGE antibodies immobilized on a suitable substrate. In this way the glycosylated proteins could be separated from the rest of the batch by conventional procedures. The substrate could be refreshed or replaced periodically in the instance of a commercial process, so that a continuous circulation of protein material past the substrate and subsequent separation of the protein-AGE component could be conducted. Naturally, the foregoing scheme is presented for purposes of illustration only, and is capable of various modifications in design and execution within the skill of the art and the scope of the invention.

The invention also includes methods for measuring protein aging both in plants and in animals, by assaying the presence, amount, location and effect of such advanced glycosylation endproducts utilizing the anti-AGE antibodies. By reacting anti-AGE antibodies with samples of products suspected of containing AGEs, plant matter and animal food samples can be evaluated to assess food spoilage and the degradation of the proteinaceous materials so affected, while the assays of animals, including body fluids such as blood, plasma and urine, tissue samples, and biomolecules such as DNA, that are capable of undergoing advanced glycosylation, assist in the detection of pathology or other systemic dysfunction.

Further, such assay may be employed to assess the extent of degradation of proteins that have been cultivated, harvested or otherwise recombinantly prepared for therapeutic use, to determine whether and/or to what extent such materials have become glycosylated. This assay could be used alone or in conjunction with a purification procedure, so that the determination that the protein material has developed a predetermined threshold level of glycosylation would signal the need for performing a purification procedure such as that described above, on a batchwise or continuous basis.

The assay methods of the invention comprise the performance of several assay protocols, involving the anti-AGE antibodies described herein whether labeled or not, the analyte, and/or a ligand, one or more binding partners to the antibody, and binding partners thereto as applicable.

The term "binding partners" is used in the general sense to refer to components used in the assays which recognize and/or bind to each other. Thus, an anti-AGE antibody and the AGEs recognized by the antibody are considered binding partners.

The term "binding partners" also includes ligands useful in the present invention, such as AGE derivatives that bind to AGE binding partners. These ligands may be detected either singly and directly, or in combination with a second detecting partner such as avidin or biotin. Suitable synthesized AGE derivatives are selected from the reaction products of reducing sugars, such as glucose, glucose-6-phosphate (G6P), fructose and ribose and peptides, proteins and other biochemicals such as BSA, avidin, biotin derivatives, and enzymes such as alkaline phosphatase.

Useful with this invention are enzymes and other carriers that have undergone advanced glycosylation. These AGE-enzymes may serve as the preferred labelled ligands in the assays of the present invention. Other suitable ligands may include the reaction product of the reducing sugars directly with carriers capable of undergoing advanced glycosylation. Suitable carriers may be comprised of a material selected from carbohydrates, proteins, synthetic polypeptides, lipids, bio-compatible natural and synthetic resins, and mixtures thereof.

The assays of the invention may follow formats wherein either the ligand or the binding partner are bound to a substrate. Likewise, the assays include the use of labels which may be selected from radioactive elements, enzymes and chemicals that fluoresce.

The present methods have particular therapeutic relevance in that means for the detection and evaluation of the condition of a broad spectrum of organ systems are provided. The Maillard process acutely affects several of the significant protein masses in the body, among them collagen, elastin, lens proteins, and the kidney glomerular basement membranes. These proteins deteriorate both with age (hence the application of the term "protein aging") and as a result of prolonged exposure to elevated blood sugar levels and AGE formation, the latter in turn frequently due to pathology.

In this manner, the location and relative concentrations of advanced glycosylation endproducts in the body can be identified. Moreover, by assaying different organ specimens, an AGE "patient profile" can be obtained, i.e., the location and relative concentration of AGEs in the patient can be identified. This technique is particularly useful in identifying abnormal concentrations of advanced glycosylation endproducts, such as in atheromatous plaques. In such manner, the location of future systemic malfunctions can be identified.

Accordingly, the present assay method broadly comprises the steps of:

A. preparing at least one sample suspected of containing said advanced glycosylation endproducts;

B. preparing at least one anti-AGE antibody directed to said samples, wherein the anti-AGE antibody is reactive with in vivo-produced advanced glycosylation endproducts and has the following characteristics:
  i. it reacts with an immunological epitope common to said in vivo-formed advanced glycosylation endproducts;
  ii. it is cross reactive with advanced glycosylation endproducts formed in vitro; and
  iii. it is not cross reactive with the following advanced glycosylation endproducts however formed: FFI, AFGP, pyrraline, and pentosidine;

C. placing a detectible label on a material selected from the group consisting of said sample, a ligand to said anti-AGE antibody and said anti-AGE antibody;

D. placing the labeled material from Step C in contact with a material selected from the group consisting of the material from Step C that is not labeled; and E. evaluating the resulting sample of Step D for the extent of binding of said labeled material.

Suitable analytes which can be evaluated may be selected from, e.g., plant matter, edible animal matter, blood, plasma, urine, cerebrospinal fluid, lymphatic fluid, and tissue; and certain synthesized compounds, individually and bound to carrier proteins such as the protein albumin. The analyte may also comprise a synthetically derived advanced glycosylation endproduct which is prepared, for example, by the reaction of a protein or another macromolecule with a reducing sugar. This reaction product can be used alone or combined with a carrier.

The carrier may be selected from the group consisting of carbohydrates, proteins, synthetic polypeptides, nucleic acids, lipids, bio-compatible natural and synthetic resins, antigens and mixtures thereof.

The anti-AGE antibodies described herein can be used both to diagnose the degradative effects of advanced glycosylation of proteins in plants, edible animal matter, and the like, and to detect the adverse effects of the buildup of advanced glycosylation endproducts. Such conditions as age- or diabetes-related hardening of the arteries, skin wrinkling, arterial blockage, and diabetic, retinal and renal damage in animals all result from the excessive buildup or trapping that occurs as advanced glycosylation endproducts increase in quantity. Therefore, the diagnostic methods of the present invention seeks to avert pathologies caused at least in part by the accumulation of advanced glycosylation endproducts in the body by monitoring the amount and location of such AGEs.

Using the present invention, one can assess and/or detect the presence of stimulated, spontaneous, or idiopathic pathological states in mammals, by measuring the corresponding presence of advanced glycosylation endproducts. More particularly, the presence or amount of the AGEs may be followed directly by assay techniques such as those discussed herein, through the use of an appropriately labeled quantity of the present anti-AGE antibodies or at least one of their binding partners, as set forth herein. Alternately, AGEs defining epitopes reactive with the present anti-AGE antibodies, could be synthesized and used to raise binding partners (or antagonists to such binding partners) that could in turn, be labeled and introduced into a medium to test for the presence and amount of AGEs therein, and to thereby assess the state of the host from which the medium was drawn.

Thus, both AGE receptors and any binding partners thereto that may be prepared, are capable of use in connection with various diagnostic techniques, including immunoassays, such as a radioimmunoassay, using for example, a receptor or other ligand to an AGE that may either be unlabeled or if labeled, then by either radioactive addition, reduction with sodium borohydride, or radioiodination.

The general assay procedures and their application are all familiar to those skilled in the art and are presented herein as illustrative and not restrictive of the procedures that may be utilized within the scope of the present invention.

The advanced glycosylation endproduct forms complexes with one or more of the binding partners, and one member of the complex may be labeled with a detectable label. The fact that a complex has formed and, if desired, the amount thereof, can be determined by applicable detection methods, e.g., IgG recognition and reaction with the complexes formed.

Suitable radioactive elements may be selected from the group consisting of $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. In the instance where a radioactive label, such as prepared with one of the above isotopes is used, known currently available counting procedures may be utilized.

In the instance where the label is an enzyme, detection may be accomplished by any of the presently utilized colorimetric, chemiluminescent, spectrophotometric, fluorospectro-photometric, thermometric, amperometric or gasometric techniques known in the art. The enzyme may be conjugated to the advanced glycosylation endproducts, their binding partners or carrier molecules by reaction with bridging molecules such as carbodiimides, diisocyanates, glutaraldehyde and the like. Also, and in a particular embodiment of the present invention, the enzymes themselves may be modified into advanced glycosylation endproducts by reaction with sugars as set forth herein.

Many enzymes which can be used in these procedures are well known and can be utilized. The preferred enzymes for detection are peroxidase, β-glucuronidase, β-D-glucosidase, β-D-galactosidase, urease, glucose oxidase plug peroxidase, hexokinase plus GPDase, RNAse, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase. U.S. Pat. Nos. 3,654,090; 3,850,752; and 4,016,043 are referred to by way of example for their disclosure of alternative labeling materials and methods.

A number of fluorescent materials are also known which can be utilized as labels. These include, for example, fluorescein, rhodamine and auramine. A particularly preferred detecting material includes one or more fluorescent labels on anti-rabbit antibodies prepared in goats and conjugated with fluorescein through an isothiocyanate.

One assay format contemplates a bound antibody to which are added the ligand and the analyte. The resulting substrate is then washed after which detection proceeds by the measurement of the amount of analyte bound to the antibody. A second format employs a bound ligand to which the antibody and the analyte are added. Both of these formats are based on a competitive reaction with the analyte, while a third format comprises a direct binding reaction between the bound analyte and the antibody. In the latter two formats, the extent of binding of the antibody is measured by a direct label or a labeled binding partner.

All of the protocols disclosed herein may be applied to the qualitative and quantitative determination of advanced glycosylation endproducts and to the concomitant diagnosis and surveillance of pathologies in which the accretion of advanced glycosylation endproducts is implicated. Such conditions as diabetes and the conditions associated with aging, such as atherosclerosis and skin wrinkling represent non-limiting examples, and accordingly methods for diagnosing and monitoring these conditions are included within the scope of the present invention.

The present invention also includes assay and test kits for the qualitative and/or quantitative analysis of the extent of the presence of advanced glycosylation endproducts. Such assay systems and test kits may comprise a labeled component prepared, e.g., by one of the radioactive and/or enzymatic techniques discussed herein, coupling a label to an anti-AGE antibody or a binding partner as listed herein; and one or more additional immunochemical reagents, one of which may be a free or immobilized ligand, capable either of binding with the labeled component, its binding partner, one of the components to be determined or their binding partner(s). One of the components of the kits described herein is typically an anti-AGE antibody in labeled or non-labeled form.

In a further embodiment of this invention, commercial test kits suitable for use in one instance by food technologists, and in other instances by medical specialists may be prepared to determine the presence or absence of advanced glycosylation endproducts. As stated earlier, the kits may be used to measure the presence of advanced glycosylation endproducts on recombinant or other purified proteins, and particularly those destined for therapeutic use, to assay them in a first instance, and in a second instance, to assist in their further purification.

In accordance with the testing techniques discussed above, one class of such kits will contain at least labeled AGE,. or its binding partner as stated above, and directions, of course, depending upon the method selected, e.g., "competitive", "sandwich", "DASP" and the like. The kits may also contain peripheral reagents such as buffers, stabilizers, etc.

Accordingly, a preferred test kit may be prepared for the demonstration of the presence, quantity or activity of AGEs, comprising:

(a) a predetermined amount of at least one labeled immunochemically reactive component obtained by the direct or indirect attachment of the anti-AGE antibodies of the present invention or a specific binding partner thereto, to a detectable label;

(b) other reagents; and (c) directions for use of said kit.

More specifically, the preferred diagnostic test kit may comprise:

(a) a known amount of a binding partner to an anti-AGE antibody as described above, or a ligand thereof, generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the preferred test kit may comprise:

(a) a labeled component which has been obtained by coupling the binding partner of the anti-AGE antibody to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the anti-AGE antibody and a specific binding partner thereto.

The present invention extends to the production of the anti-AGE antibodies in a mammal, and an antiserum containing said antibodies. For example and as illustrated herein, a mammal can be immunized with the incubation product of a reducing sugar and any protein which contains free amino groups, and which is subject to Amadori rearrangement, thus yielding AGEs.

As used herein, the terms "immunized" and "hyperimmunized" refer to the specific immunization protocol also described in detail later on herein, which is used to elicit the antibody response that yields the antiserum and antibodies of the present invention. The protein or the reaction product of the protein described above incubated with one or more reducing sugars can be used. Typically about four primary doses of the immunogen are administered to an immunocompetent mammal in an amount effective for inducing the formation of anti-AGE antibodies. Booster immunization doses may also be administered as appropriate.

The immunization of the host mammal with the protein itself or with AGEs derived from the AGE-protein, e.g., AGE-RNAse, produces antibodies which are reactive to AGEs derived from the immunogen itself or AGEs which are derived from other proteins. For example, the administration of AGE-RNAse produces polyclonal anti-AGE antibodies which react with AGE-RNAse, AGE-hemoglobin, AGE-BSA, AGE-HSA, AGE-LDL and AGE-collagen IV, but not with unmodified RNAse, BSA or HSA.

The antibodies raised as described above were also generally unreactive with model AGEs produced synthetically through procedures involving chemical hydrolysis or reduction, such as the model AGEs FFI, AFGP, pyrraline, and pentosidine. None of these model compounds was recognized by the anti-AGE antibodies raised.

The invention described herein takes advantage of the epitope which is present on these in vivo-derived AGEs and on in vitro-generated AGEs produced without specific chemical hydrolysis or reductive conditions. The epitope can be exploited in numerous processes for detecting AGEs on in vivo-derived as well as in vitro-derived material. For example, the binding affinity of anti-AGE antibodies can be used in non-competitive and competitive ELISA assays, as well as in other protocols which utilize different immunoassay configurations.

Ribonuclease modified by long-term incubation with glucose was found to be a suitable immunogen for the production of high-titre, anti-AGE antibodies against a variety of AGE-modified proteins. Advanced glycosylation endproducts prepared with glucose showed the greatest inhibition, followed by AGEs prepared with G6P and fructose. Both G6P and fructose react with proteins at a faster rate than glucose to produce brown, fluorescent AGEs.

Different glycosylating sugars such as glucose, G6P, and fructose produce antigenically cross-reactive epitopes when incubated with protein in vitro. In contrast, the purification of particular products from in vitro incubation mixtures of polypeptides or amines with glucose (FFI, AFGP, pyrraline) or from tissue glycosylated in vivo (pentosidine) resulted in compounds with no demonstrable cross-reactivity with anti-(AGE-RNAse) antiserum. This suggests that the model AGEs which have been described thus far are either antigenically minor products, or that the purification procedures which are typically used for isolating AGEs from a sample resulted in structural alterations, such that reactivity with anti-AGE antibodies is essentially eliminated.

In vitro time course studies revealed that the characteristic fluorescence of advanced glycosylation precedes the development of the anti-AGE reactive moieties. Thus, the anti-AGE antiserum appears to be most reactive with "late" advanced glycosylation endproduct(s) which form after fluorophore formation.

The ligands useful in the present invention are preferably in vivo-generated AGEs that bind to AGE binding partners. These ligands may be detected alone or in combination with a second detecting partner such as avidin and/or biotin. Suitable ligands when these signal amplifiers are used can be selected from the reaction products of reducing sugars such as glucose, G6P, fructose, ribose and the like with peptides, proteins and other biochemicals such as BSA, avidin, biotin, and enzymes such as alkaline phosphatase.

As discussed earlier herein, the invention extends to monoclonal anti-AGE antibodies which are capable of preparation by hybridoma techniques, utilizing, for example, fused mouse spleen lymphocytes and myeloma cells. Immortal, antibody-producing cell lines can also be created by techniques other than fusion, such as direct transformation of B lymphocytes with oncogenic DNA, or transfection with Epstein-Barr virus.

Specific polyclonal antibodies can be raised in different preferred host species. Naturally, these antibodies are merely illustrative of antibody preparations that may be made in accordance with the present invention.

Specific protocols are illustrated below as necessary. The protocols disclosed herein may be applied to the qualitative and quantitative determination of AGEs and to the concomitant diagnosis and surveillance of pathologies in which the accretion of AGEs is implicated. Conditions such as diabetes and those associated with aging, such as atherosclerosis and skin wrinkling, represent non-limiting examples. Accordingly, methods for diagnosing and monitoring these conditions are included within the scope of the present invention.

The biochemical and biological reagents which are recited below are available commercially or prepared in accordance with recognized protocols. All publications cited herein are hereby incorporated by reference.

MATERIALS AND METHODS

REAGENTS

The reagents used in the assays described below were obtained or prepared as follows:

Bovine pancreatic ribonuclease ("RNAse"), bovine serum albumin ("BSA"), human serum albumin ("HSA"), collagen Type 4, collagenase, glucose, glucose-6-phosphate ("G6P"), fructose, ribose, and sodium borohydride were obtained from Sigma Chemical Corp. (St. Louis, Mo.).

AGE-hemoglobin was prepared by isolating red blood cells, hemolyzing them with toluene and treating a sample of the red cell hemolysate with trichloroacetic acid (TCA). Specifically, a 50–100 µl sample of RBC hemolysate was prepared and 3 ml of water and 1 ml of 24% (wt/vol) TCA were added. The mixture was agitated, and thereafter centrifuged for 30 minutes at 3000 rpm. The resulting supernatant was aspirated, 150 µl 1N NaOH was then added, after which water was added to a total volume of 0.5 ml. This material was then diluted from 1:2 to 1:200 with 0.3M $KH_2PO_4$ pH 7.4, and was prepared for performance of the assay.

AGE-albumin was prepared by incubating albumin (50 mg/ml) with 0.5M glucose, G6P or fructose in 0.2 M $NaPO_4$ buffer (pH 7.4) for 60 days.

AGE-collagen was synthesized by incubating collagen (5 mg/ml) with 0.5 M glucose in 0.2 M $NaPO_4$ buffer (pH 7.4) for 21 days.

AGE-RNAse was prepared by incubating RNAse (25 mg/ml) with 1 M glucose in 0.2 M $NaPO_4$ buffer (pH 7.4) for 90 days.

FFI-BSA was prepared by coupling FFI-hexanoic acid to BSA with carbodiimide.

Formaldehyde-BSA, maleyl-BSA and acetyl-LDL were synthesized in accordance with the procedures described in Horiuchi, S. et al., J. BIOL. CHEM., 4:260, 432, 438 (1985);

Takata, K. et al., BIOCHIM. BIOPHYS. ACTA., 94:273–280 (1989); and Goldstein, J. L. et al., PROC. NATL. ACAD. SCI. USA, 77:333–337 (1979).

AGE-LDL was prepared according to a protocol in which spontaneous oxidation is minimized, according to Kirstein, M. et al, PROC. NATL. ACAD. SCI. USA, 87:9010–9014 (1990).

AGE-BSA was reduced with sodium borohydride as described in Flückiger, R. et al, METHODS ENZYMOL., 106:77–87 (1984). Any unreacted borohydride was removed by dialysis against PBS.

For aminoguanidine inhibition, BSA (100 mg/ml) was incubated with 100 mM glucose and 100 mM aminoguanidine hydrochloride (Aldrich Chemical Co., Milwaukee, Wis.) in 0.2 M $NaPO_4$ buffer (pH 7.4) for 21 days at 37° C. Samples were dialyzed against PBS prior to analysis.

Lysine-derived AGEs were prepared by incubating 1 M glucose-6-phosphate or 1 M glucose with 50 mM L-lysine in 0.2 M sodium phosphate buffer (pH 7.4) 10 days at 37° C.

1-deoxy-1-morpholino-D-fructose was obtained from Sigma Chemicals, Inc. and 1-deoxy-1-propylamino-D-fructose was prepared from an d-D-glucose and N-propylamine according to Mitchel, F. et al., CHEM. BER., 92:2836–2840 (1959). 2-(2-furoyl)-4(5)-(2-furanyl)-1H-imidazole) was synthesized from an aqueous mixture of furylglyoxal and 6-aminohexanoic acid and purified by medium pressure chromatography on silica gel.

1-alkyl-2-formyl-3,4-diglycosyl-pyrrole (AFGP) was prepared by incubating glucose with 6-aminohexanoic acid and sodium sulfite for 26 days at 37° C. followed by chromatography on Dowex AG 1×4 anion exchange resin and HPLC.

OTHER METHODS

The anti-AGE antibody and its reactivity with in vivo-derived AGEs, and its non-reactivity with AGEs synthesized chemically by methods involving hydrolysis or reduction were evaluated. Protein concentrations were determined in accordance with Bradford, M., ANAL. BIOCHEM., 72:248–252 (1976), and BSA was utilized as a standard. Ribonuclease and AGE-RNAse protein amounts were determined additionally by SDS-PAGE and comparison of Coomassie Blue stained bands with RNAse standards. Hydroxyproline content was determined according to Edward, C. et al., CLIN. CHIM. ACTA, 104:161–167 (1980). Collagen AGE-specific fluorescence determinations were performed by measuring emissions at 440 nm upon excitation at 370 nm using an LS-3B fluorescence spectrometer (Perkin-Elmer, Norwalk, Conn.).

A preparation of control albumin was also incubated under the same conditions described above without sugar. All incubations were performed under sterile conditions in the dark, and at 37° C. After incubation, unbound material was removed by extensive dialysis against phosphate buffered saline (PBS) or by gel filtration over Sephadex G-10 (Pharmacia, Uppsala, Sweden).

A single standard AGE-BSA preparation (1 mMAGE-BSA=12 $A_{350}$) was used as a reference. Fluorescence intensity standards were used to calibrate and monitor the performance of the instrument. Fluorescence values of test substances were measured at a protein concentration of 1 mg/ml and expressed as percent relative fluorescence compared to the AGE-BSA standard.

PRODUCTION OF ANTI-AGE ANTIBODIES

Previous efforts to raise antisera against native AGEs generally have been unsuccessful or have failed to detect AGEs which occur in vivo.

To induce the formation of anti-AGE antibodies, synthesized AGEs were produced in vitro as described above without resort to hydrolytic or chemical reduction reactions. The protein was typically incubated with a reducing sugar to form AGEs.

Glucose was preferably used as the glycosylating agent in vitro because it is the major circulating sugar and it produces AGEs in vitro which closely resemble the AGEs which are formed in vivo. RNAse was selected as the target protein for advanced glycosylation because RNAse readily forms AGEs and AGE-mediated intermolecular crosslinks.

Two female New Zealand White rabbits received four primary immunizations and one booster immunization of RNAse or AGE-RNAse emulsified in Freund's complete adjuvant following a protocol for post-translationally modified proteins in accordance with R. Bucala, et al., Mol. Immunol., 20:1289–1292 (1983) ("hyperimmunization protocol") and as follows. Accordingly, each rabbit received four intradermal injections over the back (200 µg each) and one injection in each hind quarter (100 µg each). This procedure was repeated at weekly intervals for six weeks. After a two week rest, the rabbits received a booster injection of 1 mg of antigen in Freund's incomplete adjuvant. The amimals were bled on the tenth day after this injection. Antibody response was monitored weekly by Ouchterlony double diffusion and by non-competitive ELISA.

Using the hyperimmunization protocol described above, high titre polyclonal rabbit anti-serum against RNAse (the carrier protein) was obtained. The anti-RNAse titre was determined to be greater than $10^{-5}$ in a non-competitive ELISA. The following absorbed antigens were tested: RNAse, glucose-derived AGE-RNAse, BSA, glucose-derived AGE-BSA and G6P-derived AGE-BSA. The results are shown below in FIG. 1.

Significantly higher reactivity was observed for the immunogen AGE-RNAse than RNAse. The anti AGE-RNAse antiserum also reacted with albumin modified by incubation with either glucose or G6P, but not with unmodified albumin, indicating the presence of antibodies specific for AGEs.

EXAMPLE 1

ELISA ASSAYS

To monitor the formation of anti-AGE antibodies, rabbit antiserum produced as described above, was titered in a non-competitive ELISA system. RNAse, AGE-RNAse, and AGE-BSA were used as the absorbed antigens.

The absorbed antigen was contacted with rabbit serum, allowing the anti-AGE antibodies contained in the serum to complex. The level of complex formed was then evaluated by adding anti-rabbit IgG antibodies conjugated to alkaline phosphatase (Organon Technica, Durham, N.C.). The titre for anti-(AGE-RNAse) antiserum was thereafter defined as the serum dilution giving a 50% of maximum $OD_{405}$ signal.

Ligand inhibition and AGE measurements were then performed in competitive ELISA. Ninety-six well microtitre plates (Nunc Immunoplate, Gibco, Grand Island, N.Y.) were coated with AGE-BSA (obtained as described above) by adding 0.1 ml of a solution of AGE-BSA (10 µg/ml, dissolved in PBS) to each well and incubating for 2 hrs. at room temperture. Wells were then washed three times with 0.15 ml of a solution containing PBS, 0.05% Tween-20, and 1 mM $NaN_3$ (PBS-Tween).

The wells were blocked by incubation for 1 hour with 0.1 ml of a solution of PBS containing 2% goat serum, 0.1%

BSA, and 1 mM NAN.. After washing the blocked wells with PBS-Tween, 50 µl of a competing antigen was added, followed by 50 µl of the rabbit-derived antiserum (final dilution, 1/1000).

Plates were thereafter incubated for 3 hours at room temperature, after which the wells were washed with PBS-Tween and developed with an alkaline phosphatase linked anti-rabbit IgG (raised in goats) utilizing p-nitrophenylphosphate as the colorimetric substrate.

Results were expressed as B/Bo, wherein Bo is the maximum amount of antibody bound in the absence of competing antigen, and B is the amount of antibody bound in the presence of competing antigen. Both Bo and B have been adjusted for background (See Robard, CLIN. CHEM., 20:1255–1270 (1974) and calculated as [experimental optical density at 405 nm—background optical density (no antibody)]/[total (no competitor)—background optical density].

It was determined that three micrograms of the glucose-derived AGE-BSA standard inhibited antiserum binding by 50%. This standard yielded an $A_{350}$ of 12 $mM^{-1}$ albumin.

Figure 2A:
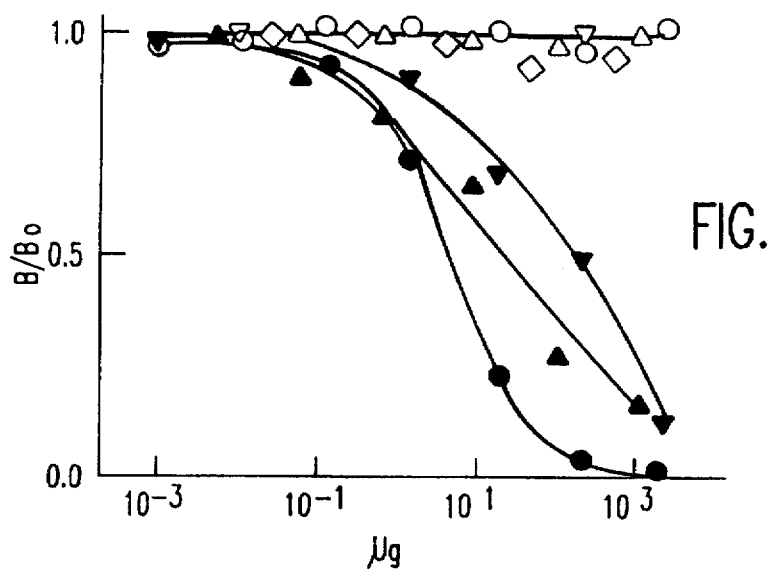
FIG. 2A–2C are ELISA competition curves for anti-AGE-RNAse antiserum. Assays were performed as described in Materials and Methods and employed glucose-derived AGE-BSA as the absorbed antigen. All points represent the mean of triplicate determinations.

The specificity of the anti-(AGE-RNAse) antiserum was thus tested using a variety of AGE-modified proteins, unmodified proteins, and synthetic AGEs. As shown in FIG. 2A (A) results were obtained by testing anti-(AGE-RNAse) antiserum against different modified albumins in a competitive ELISA system using AGE-BSA as the absorbed antigen. All points represent the mean of triplicate determinations.

The AGE-albumin prepared by incubation of BSA with glucose showed the greatest inhibition, followed by AGE-albumin prepared with glucose-6-phosphate and with fructose.

FFI-BSA, a BSA derivative which carries the synthetic AGE ligand FFI, was not recognized by the antiserum. Other albumin modifications such as formylation or maleylation, which produce specific recognition signals for albumin uptake in vivo likewise did not demonstrate any cross-reactivity with the antiserum.

Figure 2B:
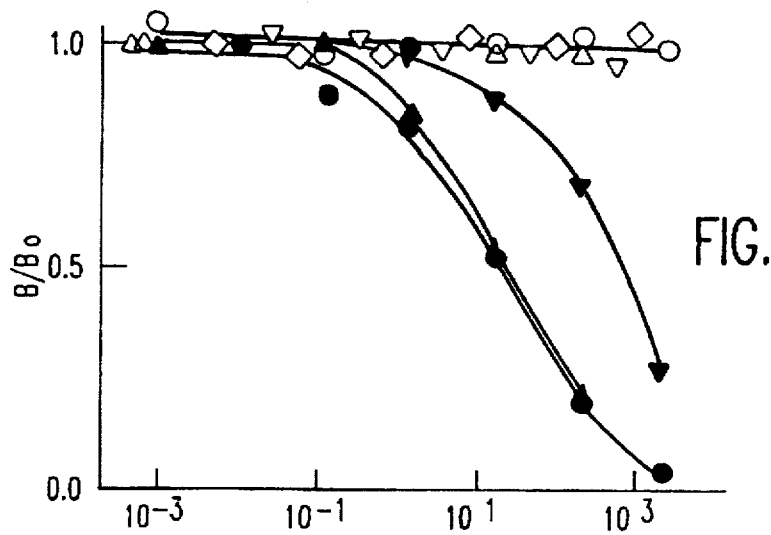

The AGE-modification competed for antibody binding in the competitive ELISA when it was present on diverse carrier proteins (FIG. 2B). Thus, G6P-derived AGE-HSA, glucose-derived AGE-LDL, and glucose-derived AGE-collagen (type IV), all demonstrated specific inhibition of antibody binding to glucose-derived AGE-BSA. In contrast, unmodified HSA, unmodified LDL, and unmodified collagen did not so compete. Acetyl-LDL, a modified form of LDL which is specifically recognized and taken up by cellular scavenger receptors, also was not recognized by the anti-(AGE-RNAse).

Figure 2C:
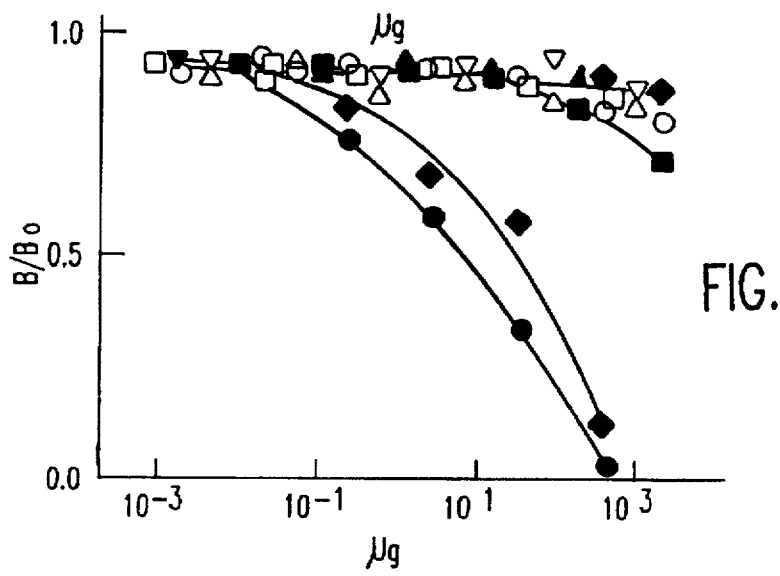

The anti-AGE antiserum was also tested for competition against model, structurally defined AGEs (FIG. 2C). The model AGE products tested were FFI, AFGP, pyrraline, carboxymethyllysine, and pentosidine. These compounds were isolated from in vitro incubations of amines with reducing sugars or from tissue collagen after reduction and acid hydrolysis. These compounds were tested at high concentrations so that even low levels of inhibition would be readily detected. None of these products competed with the binding of the antiserum to AGE-BSA, with the exception that at very high concentrations, carboxymethyllysine demonstrated some inhibitory activity. This activity, while demonstrating a trend toward inhibition, was not highly significant. Nevertheless, the data could not conclusively rule out some reactivity with carboxymethyllysine.

Glucose and G6P were incubated with lysine to determine whether low molecular weight AGEs could react with the antiserum obtained. These products were generated by the incubation of glucose or G6P with lysine in vitro without chemical reduction or hydrolysis. The resulting product was tested for reactivity in the competitive ELISA.

Control incubations consisting of either sugar or lysine alone failed to show any competition (data not shown). Two model Amadori products, deoxypropylaminofructose and deoxymorpholinofructose were also tested, and each compound failed to inhibit antiserum binding. Further evidence that Amadori products are not recognized by the antiserum was provided by the fact that sodium borohydride reduction of AGE-BSA did not diminish reactivity in the competition ELISA (data not shown).

Figure 4:
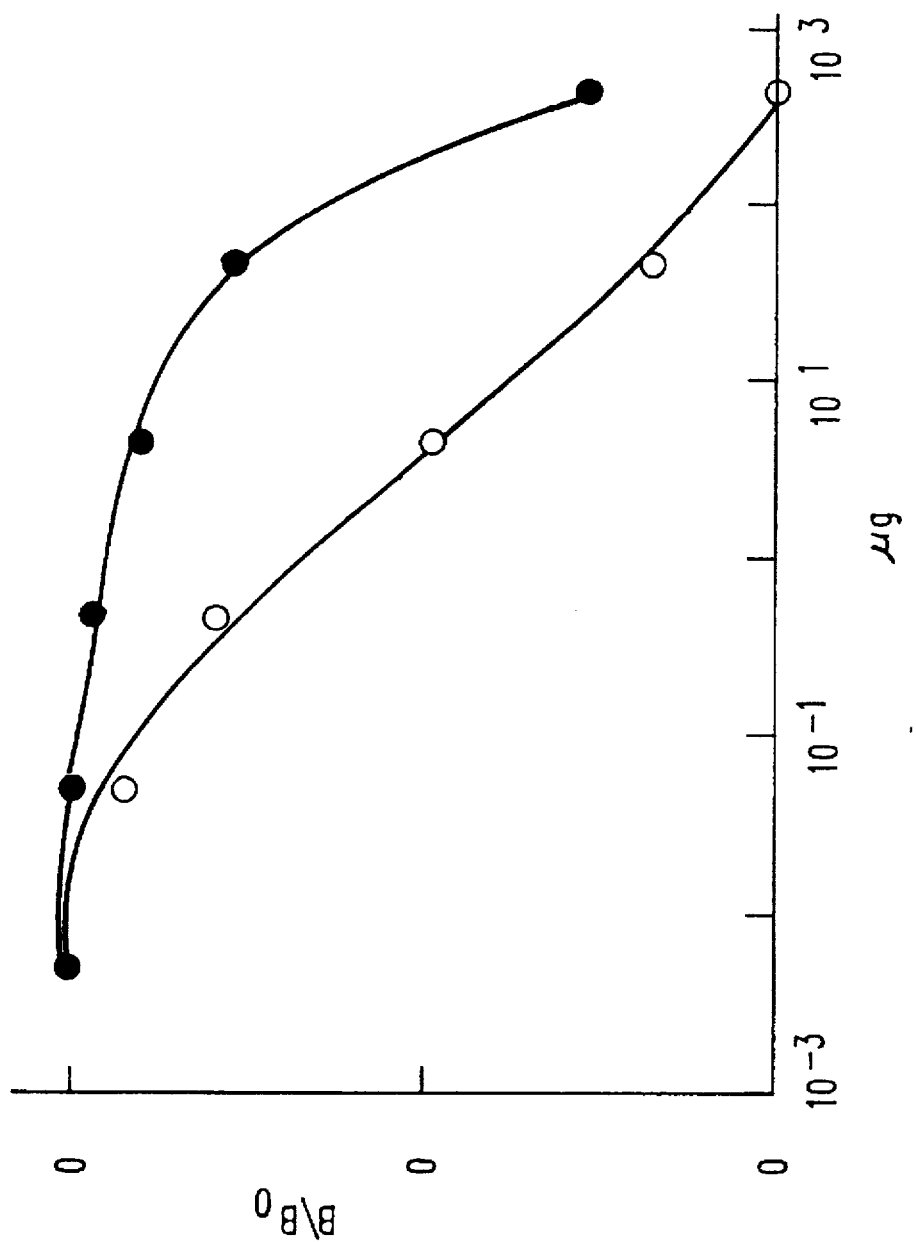
FIG. 4 is the inhibition of the formation of antibody-reactive AGEs by aminoguanidine. BSA (100 mg/ml) incubated with glucose (100 mM) for 21 days at 37° (○). BSA (100 mg/ml) incubated with glucose (100 mM) in the presence of 100 mM aminoguanidine for 21 days at 37° (●). Buffer conditions were as described in Materials and Methods.
Figure 5A:
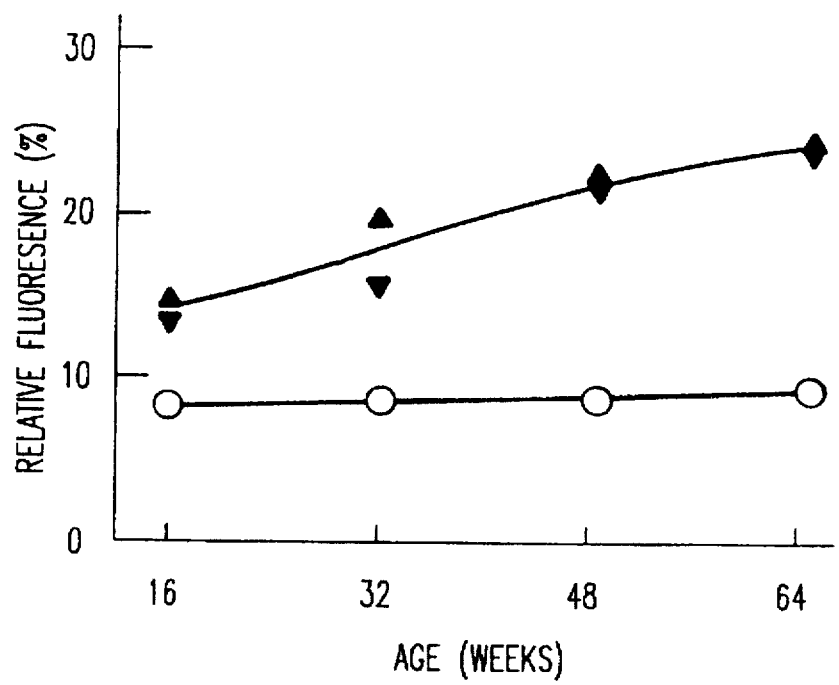
FIG. 5A–5B are the determination of AGE-collagen in experimental rats. Diabetes was induced in Lewis rats with either alloxan or streptozotocin as described in Materials and Methods. At 16 week intervals, 6 animals were sacrificed and the aortic collagen analyzed for hydroxyproline, fluorescence, and AGE-content by ELISA. Values are expressed per mg of hydroxyproline.
Figure 5B:
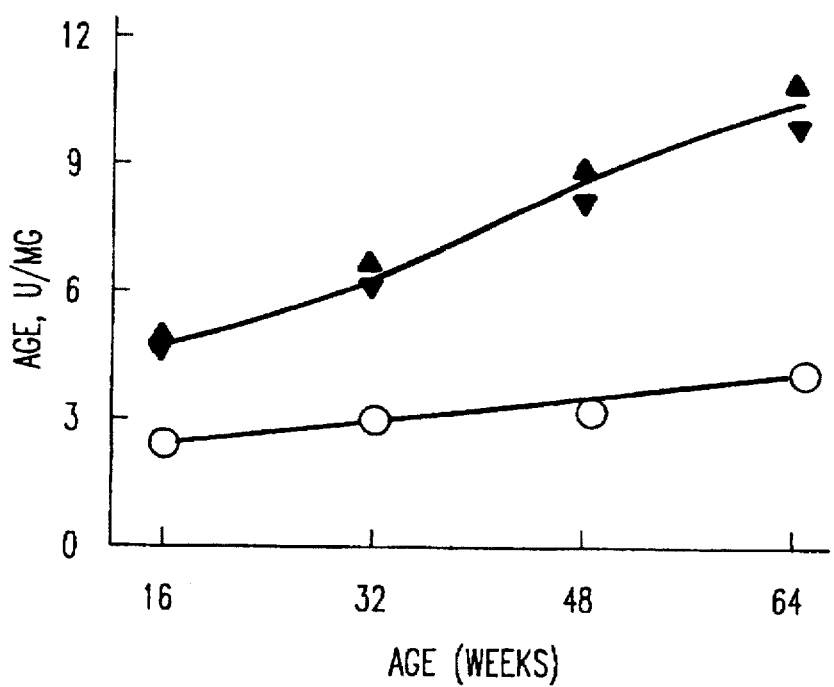
Figure 6:
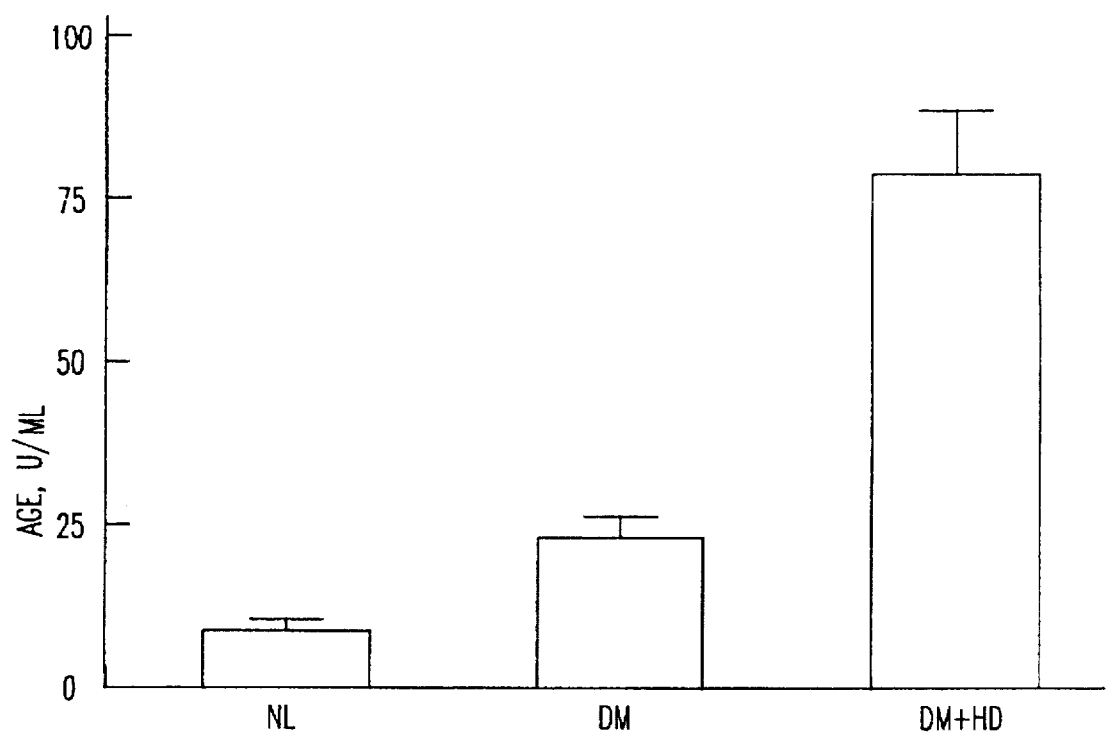
FIG. 6 is the determination of human serum AGE levels. NL: Normal individuals (n=12). DM: Diabetic individuals (n=21). DM+HD: Diabetic individuals on hemodialysis (n=16). Error bars show the S.E.M. P<0.001 for DM rs. NL. P<0.001 for DM+HD rs. DM.

To further characterize the nature of the in vivo-generated AGEs which react with the anti-(AGE-RNAse) antiserum, AGEs were synthesized in the presence of the advanced glycosylation inhibitor aminoguanidine. Aminoguanidine is a hydrazine-like compound which reacts at an intermediate stage of the advanced glycosylation process, inhibiting the formation of protein-bound fluorescent products and crosslinks. As shown in FIG. 4, the inclusion of aminoguanidine in an in vitro incubation of glucose and BSA significantly inhibited the formation of AGEs which react and bind to the anti-AGE antiserum.

EXAMPLE 2

AGE FORMATION KINETICS

Figure 3:
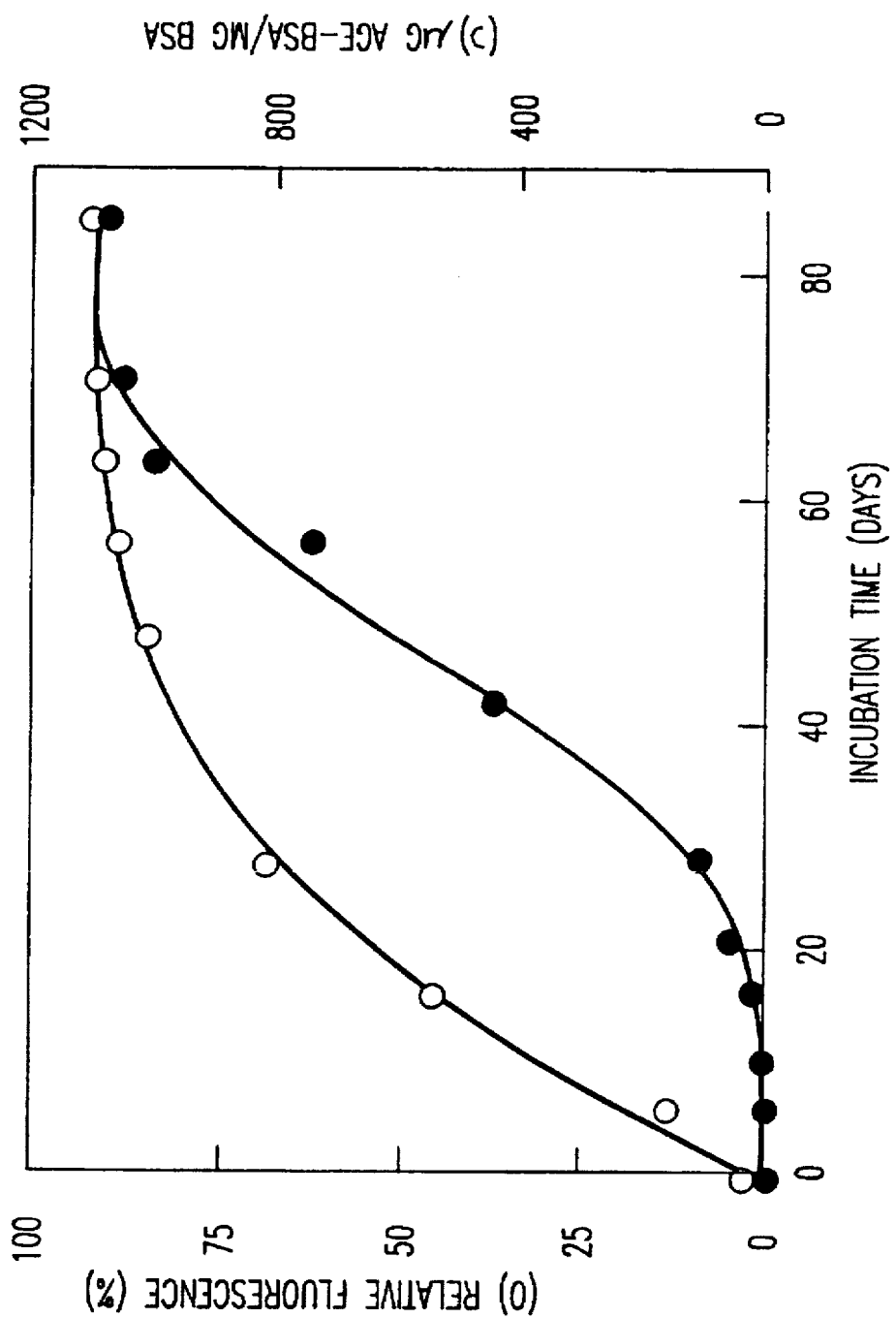
FIG. 3 is the kinetic relationship between the formation of AGE-associated fluorescence and antibody reactive material. BSA (50 mg/ml) was incubated with glucose (0.5 M) as described in Materials and Methods. Aliquots were sampled at indicate times, dialyzed to remove unbound material, and assayed for fluorescence ($\lambda_{excitation}$=370 nm, $\lambda_{emission}$=440 nm) and AGE content by ELISA.

The kinetic relationship between the formation of AGE-associated fluorescence and the formation of products which bind to anti-AGE antiserum was also evaluated. FIG. 3 shows a time course for the development of fluorescence and anti-AGE antibody reactive material. BSA was incubated with glucose, aliquots were removed at various intervals, dialyzed to remove unbound products, and then assayed. AGE-fluorophores were observed to form rapidly between 0 and 40 days and to precede the formation of antibody reactive products.

When measured by ELISA, AGEs were not detected until day 20, and then formed rapidly between days 30 and 70. The formation of both AGE fluorophores and antibody reactive products eventually plateaued.

EXAMPLE 3

DIABETES EVALUATION

As stated above, the present invention affords a particularly effective means for the detection and evaluation of diabetes as well as other disease states in which AGE levels are abnormal. Effective assessment of the presence and/or quantity of AGEs in diabetic tissue, and the use of the AGE assays described herein to characterize the overall condition of a mammal known to be diabetic, are described below.

To determine whether tissue AGEs could be measured by anti-AGE ELISA, rats with experimentally-induced diabetes mellitus were evaluated.

Diabetes was induced in 8-week-old male Lewis rats by the rapid intravenous injection of alloxan (40 mg/kg) or streptozotocin (65 mg/kg). Hyperglycemia was confirmed by assaying blood glucose. Blood glucose was determined at 16 week intervals and averaged 20.5±2.4 mM in the alloxan-treated animals (n=24) and 23.5±3.9 in the streptozotocin-treated animals (n=24). There was no significant change in blood sugar levels with time in the control, alloxan-treated, or streptozotocin-treated animals.

At 4 month intervals, 6 animals were sacrificed and the aortas removed and frozen at −80° C. for later analysis.

Arterial tissue was slowly thawed, rinsed with PBS, and finely minced with scissors. Lipids were extracted with acetone/chloroform (1:1) by shaking gently overnight at 4° C. Samples then were dried by vacuum centrifugation and resuspended in 0.2 M NaPO$_4$ buffer (pH 7.4). Collagenase (Type VII) was then added at a 1/100 (w/w) ratio and the mixture incubated for 48 hr at 37° C. with mild shaking. One drop of toluene was included to maintain sterility. Digested samples then were centrifuged at 15,000×g and the clear supernatants used for fluorescence, AGE, and hydroxyproline measurements.

In the diabetic animals (alloxan-plus-streptozotocin group), relative fluorescence increased from 13.7%±2.4% at 16 weeks to 23.7%±3.0% at 64 weeks (P<0.001).

Fluorescence in the control, non-diabetic animals increased slightly during this time period (8.3%±1.0% to 9%±0.8%, not statistically significant). Tissue and serum AGE values were expressed as AGE Units. One AGE Unit was defined as the amount of antibody-reactive material that was equivalent to that in 1 µg of the AGE-BSA standard. The P values were calculated by the unpaired Student's t-test for comparison between groups.

Analysis of the AGE content by ELISA showed an approximately two-fold increase with time in the diabetic animals (4.8±0.5 U/mg at 16 weeks versus 10.5±1.8 U/mg at 64 weeks, P<0.001). Arterial AGE content also increased with time in the control, non-diabetic rats although at a much lower rate than in the diabetic animals (2.5±0.6 U/mg at 16 weeks versus 4.3±0.4 U/mg at 64 weeks P<0.001).

Human serum was also obtained from normal and diabetic patients. Patients with compromised renal function were also studied because this group of patients has been found to have markedly elevated levels of circulating, serum AGEs.

These circulating, serum AGEs are primarily in the form of low-molecular peptides which are inefficiently cleared by hemodialysis therapy.

Serum samples were obtained from non-diabetic (n=12), diabetic (n=21), and diabetic patients on hemodialysis (n=16). Serum was diluted three-fold with PBS and filter sterilized through a 0.22 µm Millipore filter. (Millipore, Bedford, Mass.) prior to analysis.

When expressed as AGE U/ml, the normal patients (non-diabetic, normal renal function) had a mean level of 10.5±1.3 U/ml serum. The AGE levels were elevated more than two-fold in the diabetic patients (24.7±2.4 U/ml, P<0.001 for diabetic (DM) vs. normal (NL) and almost eight-fold in diabetic patients on hemodialysis (79.4±9.9 U/ml, P<0.001 for DM+HD vs. DM). These results correlate well with the findings of a recent study which utilized a radioreceptor assay to measure the AGE-peptide content of serum obtained from diabetic patients and from diabetic patients on hemodialysis.

EXAMPLE 4

An assay of time-integrated blood glucose levels was performed using the protocol followed in Example 3 above, with samples taken from normal and diabetic patients. The results of the assay were compared against values that are received when time-integrated blood glucose is measured using the known standard of HbA$_{1c}$, and are presented in FIGS. 7 and 8A–8B.

Figure 7:
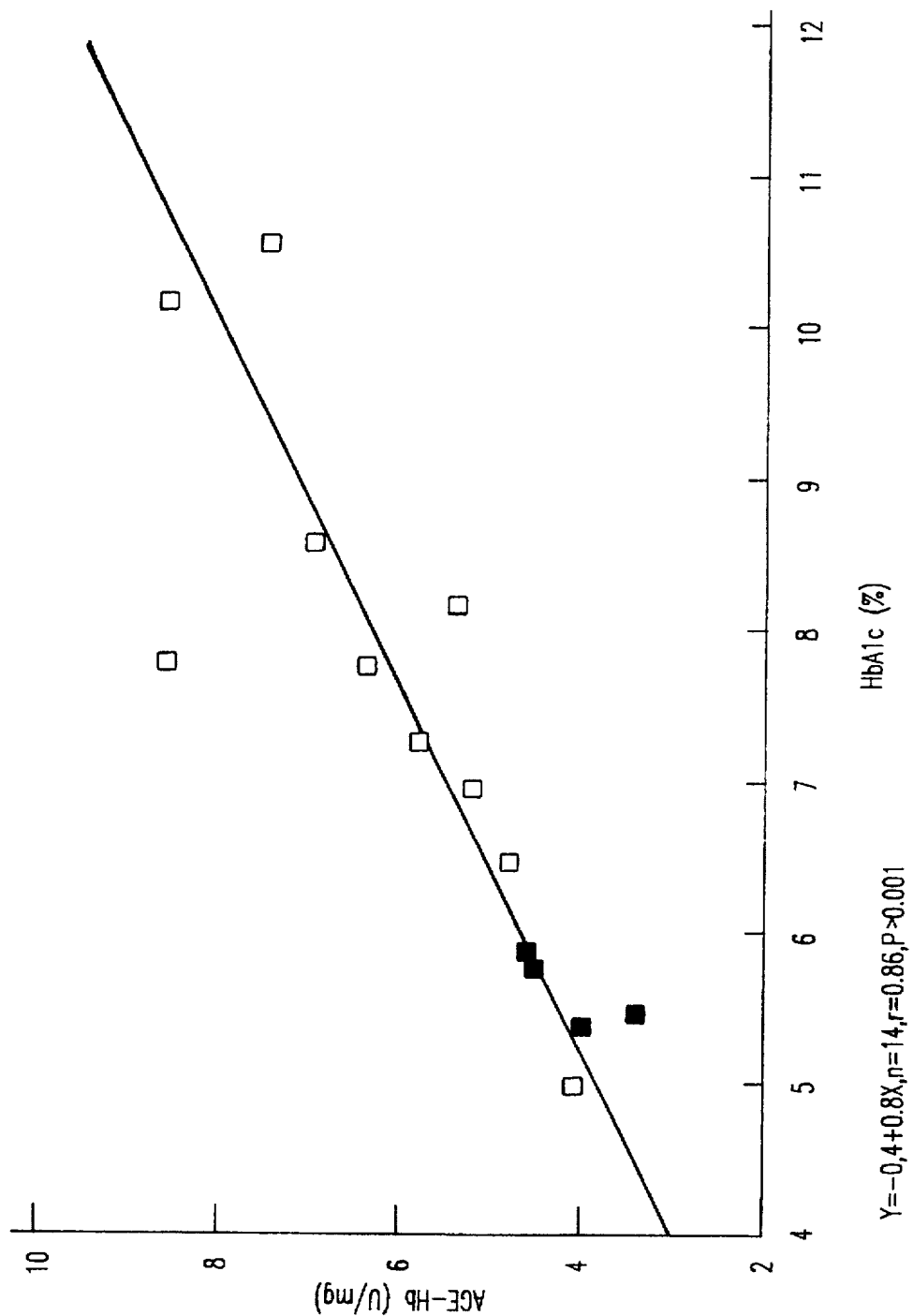
FIG. 7 is a graph comparing Hb-AGE and $HbA_{1c}$ levels in red blood cells of normal and diabetic patients and thereby depicting the correlation between the two (normal patients= ■) (diabetic patients=□)
Figure 8:
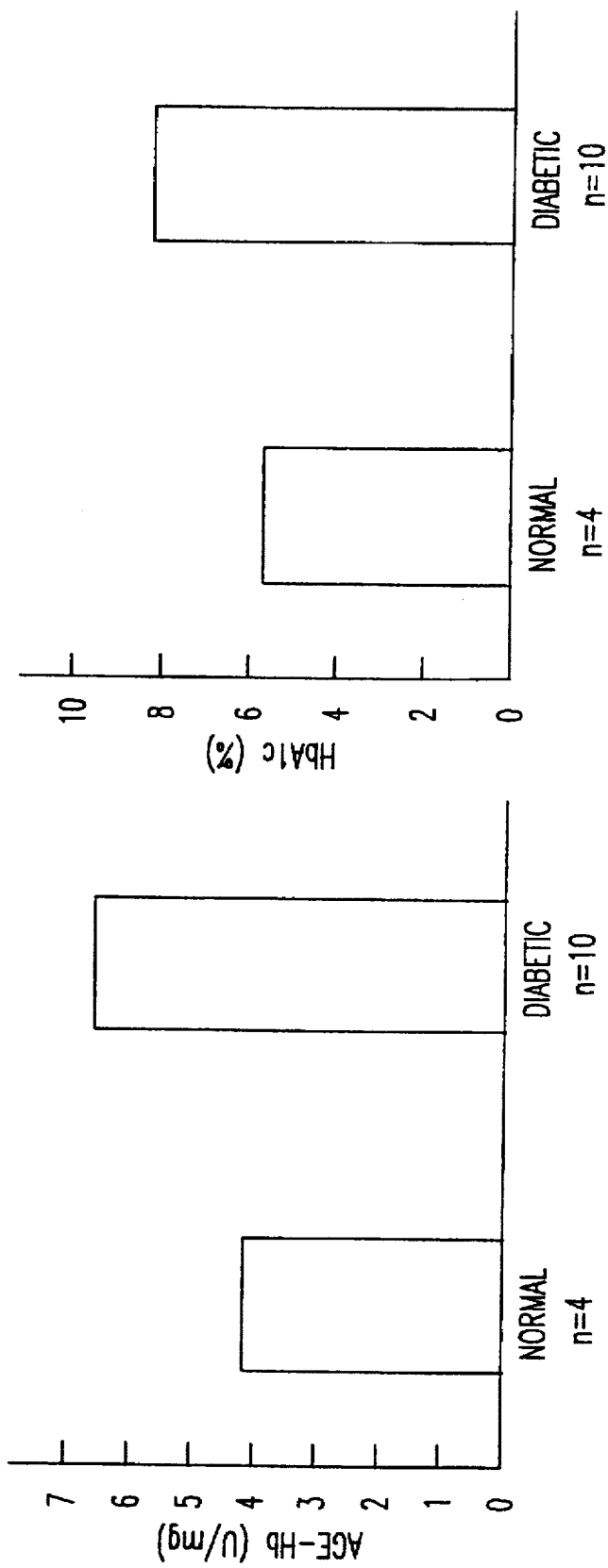
FIG. 8A–8B comprise two bar graphs that show and compare the mean of Hb-AGE (FIG. 8A) and $HbA_{1c}$ (FIG. 8B) levels in normal and diabetic patients.

Referring to FIGS. 7 and 8A–8B, it can be seen that the performance of the present assay with AGE-hemoglobin as the standard compares favorably with the known determinant and standard HbA$_{1c}$, and can be used in any instance where the latter test may be called for. The data measurements that were received are virtually identical and the clinical integrity of the present assay is consequently high.

A further diagnostic application of the present invention is in the measurement of fructose-derived AGEs. The measurement of fructose-derived AGEs is being recognized as a significant determinant of the rate of AGE formation, and the concomitant development and extent of the pathologies and other sequelae that have been associated with this reaction, such as diabetes mellitus. Suarez et al., (1989) J. BIOL. CHEM., 264:3674–3679, and McPherson et al., (1988) BIOCHEMISTRY, 27:1901–1907, both suggest that the presence and participation of fructose in protein crosslinking fortells a significant role for fructose-derived AGEs that commends its measurement and control, and significantly, Ahmed et al., (1992) CLIN. CHEM., 38(7):1301–1303, state that fructosylated Hb is incapable of effective diagnosis by presently known clinical assays.

Accordingly, the present invention is appropriately extended to the measurement of fructose-derived AGEs in a comprehensive effort to better understand and treat the adverse effects of the reaction of the accumulation of fructose-derived AGEs with body proteins.

EXAMPLE 5

Anti-AGE antibodies developed for the detection of in vivo-formed AGEs were used in a competitive ELISA to measure hemoglobin-linked AGEs in red cell hemolysates. FIG. 9 shows the results of this analysis for 32 red cell samples obtained from diabetic individuals (DM) and non-diabetic normoglycemic individuals (NL). Hemoglobin-linked AGEs were detected in both groups of individuals, but significantly higher amounts were present in the diabetic group (NL [n=9]:4.3±0.3 Units AGE/mg Hb; DM [n=23]:7.7±0.6 Units AGE/mg Hb, [Mean±S.E.], P<0.001 by Student's unpaired t-test).

Antibody reactivity, expressed in AGE Units, was calculated relative to a synthesized AGE-albumin standard. Additional experiments showed that the hemoglobin-AGE modification is stable to dialysis, acid precipitation and proteolysis, and is unaffected by borohydride reduction (data not shown). These data, together with previous studies of anti-AGE antibody specificity confirm that the hemoglobin-AGE moiety is a stable glucose-derived post-Amadori product. The levels of red cell HbA$_{1c}$ correlate with the levels of Hb-AGE in a statistically significant manner.

EXAMPLE 6

Figure 11:
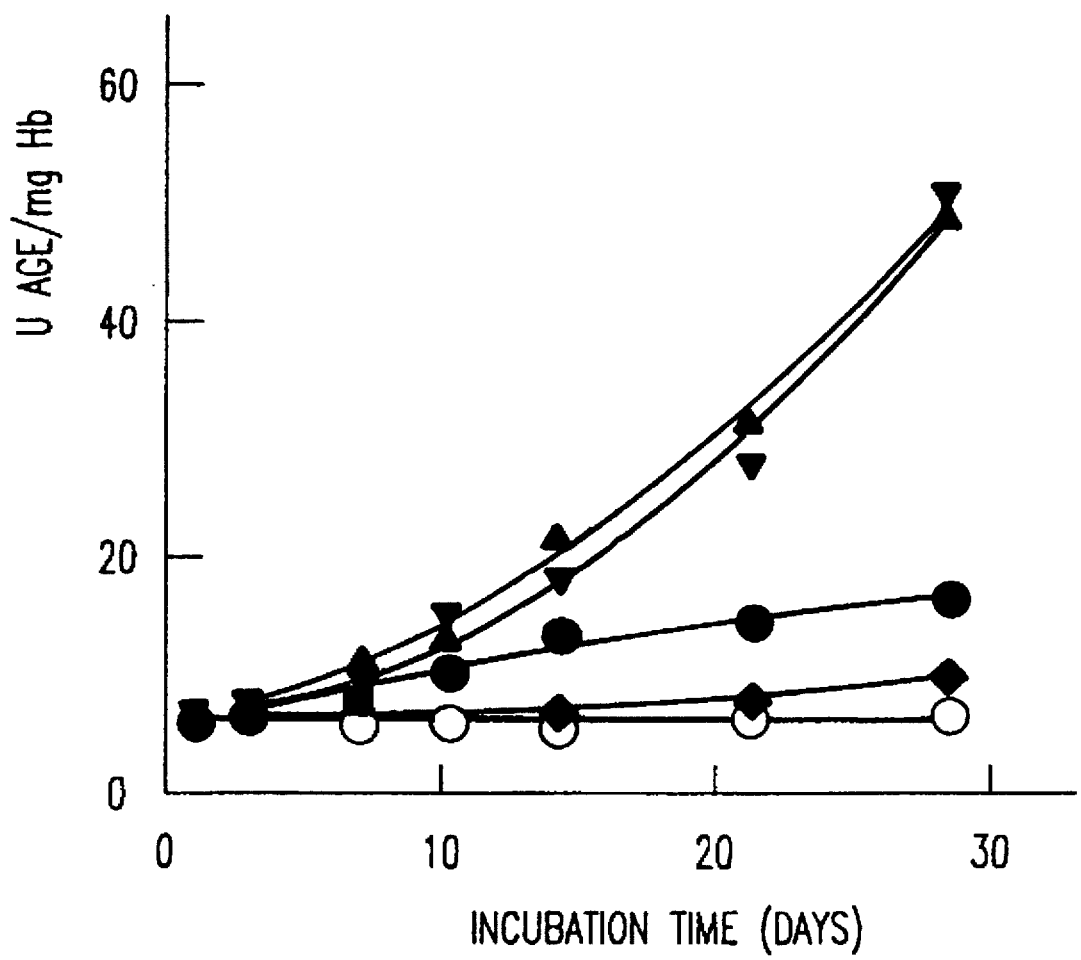
FIG. 11 is a graph of Hb-AGE formation in vitro. Human hemoglobin (50 mg/ml) (Siena Chemical Co.) was incubated at 37° C. in 0.4 M NaPO$_4$ buffer (pH 7.4) containing 0 mM glucose (○), 5 mM glucose (●), 20 mM glucose (▲), or 20 mM glucose and 50 mM aminoguanidine (♦). Aliquots containing hemoglobin and 20 mM glucose were reduced with a 200-fold molar excess of sodium borohydride prior to ELISA (▽). Aminoguanidine (50 mM) also inhibited (>95%) Hb-AGE formation in the 5 mM glucose condition (data not shown). Aminoguanidine (50 mM) did not inhibit the detection of Hb-AGE when added to glucose/hemoglobin incubations 1 hour prior to ELISA analysis (data not shown). All incubations were performed after sterile filtration. One ml samples were removed at the indicated time points and dialyzed against phosphate-buffered saline prior to ELISA analysis.

The formation of Hb-AGE from hemoglobin and glucose was confirmed in vitro. Purified human hemoglobin was incubated at 37° C. with glucose concentrations that mimicked normoglycemia (5 mM) and hyperglycemia (20 mM). Hemoglobin-AGE formed in a time and concentration dependent manner. See FIG. 11. That early Amadori glycation products are unreactive with anti-AGE antibodies was confirmed in the present system by the observation that sodium borohydride reduction which alters the Amadori product epitope did not affect the detection of Hb-AGE products once formed. The addition of aminoguanidine prevented the formation of hemoglobin-associated AGEs.

Figure 12:
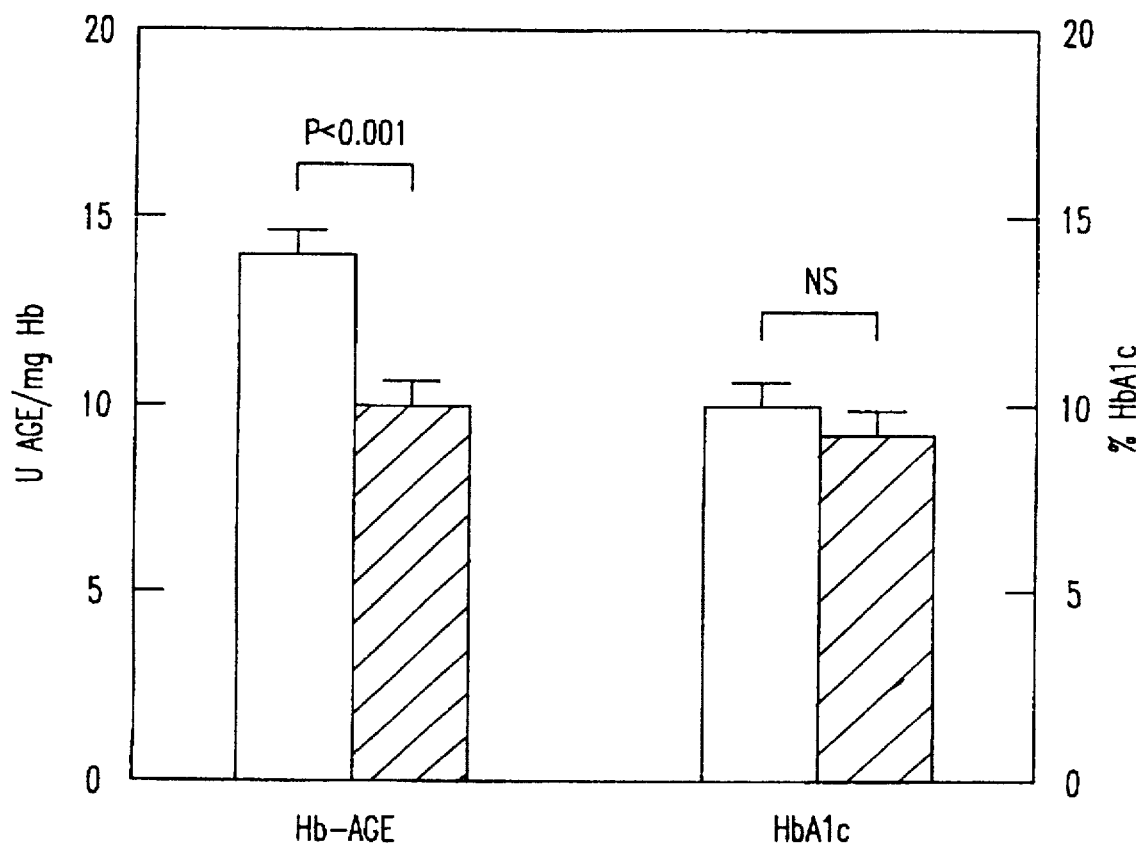
FIG. 12 is a determination of Hb-AGE and $HbA_{1c}$ levels in 18 diabetic patients before (■) and after (☰), 28 days of aminoguanidine therapy. Hb-AGE: 13.8±0.8 U AGE/mg Hb–>10.0±0.9 U AGE/m, Hb; $HbA_{1c}$: 10.1%±0.8%–>9.2% ±0.8% (Mean±S.E.).

Hemoglobin-AGE measurements were performed in blood specimens obtained from patients undergoing treatment with aminoguanidine. The patient group consisted of 18 individuals with long standing diabetes mellitus. Blood samples were obtained before and after 28 days of aminoguanidine treatment and the Hb-AGE levels were determined by ELISA. As shown in FIG. 12, the mean Hb-AGE value decreased significantly as a result of aminoguanidine therapy. (13.8±0.8 Units AGE/mg Hb vs. 10.0±0.9 Units AGE/mg Hb [Mean±S.E.] P<0.001, by Student's paired t-test).

$HbA_{1c}$ values were not affected by aminoguanidine treatment (10.1% ±0.8% v. 9.2%±0.8%, [Mean±S.E.] P=NS). No significant changes in either the Hb-AGE or $HbA_{1c}$ levels were observed in blood samples obtained from a group of six patients receiving a placebo control (data not shown).

The existence of an AGE-modified hemoglobin is noteworthy in several respects. First, AGEs generally have been considered to require a time course of months to years to form, even under hyperglycemic conditions. The present findings indicate that within the lifespan of circulating red cells, e.g. about 120 days, significant amounts of AGE-modified hemoglobin are formed. If Hb-AGE Units, expressed relative to a synthetic AGE-albumin standard, are recalculated as a fraction of total red cell hemoglobin, Hb-AGE appears to account for 0.42±0.07% of circulating hemoglobin. This level increases to a mean of 0.75±0.08% in the diabetic group that was studied. These values contrast with corresponding $HbA_{1c}$ fractions of 5.8% and 8.9% for the normoglycemic and diabetic groups respectively.

The high amount of AGE accumulation on hemoglobin compared to connective tissue or basement membrane collagen may reflect the receptor-mediated turnover of connective tissue AGEs during normal remodeling or indicate an inherently enhanced rate of AGE formation on hemoglobin as a protein substrate. Alternatively, circulating red blood cell hemoglobin may be susceptible to modification by reactive plasma AGEs which occur in elevated amounts in patients with diabetes, renal insufficiency or other disease conditions. Irrespective of the mechanism of formation, the application of quantitative ELISA methods to measurements of in vivo-generated AGEs indicates that AGE formation occurs more rapidly with hemoglobin than with connective tissue collagen.

Hb-AGE may thus serve as a useful biochemical index of advanced glycosylation in vivo. The formation of Hb-AGE reflects a time integral of blood glucose concentration that is significantly longer than that established for $HbA_{1c}$ (3-4 weeks). Four week pharmacological intervention with aminoguanidine was sufficient to lower significantly (28%) the Hb-AGE levels in a treated diabetic population.

Hb-AGE measurements may facilitate a variety of investigations into the pathophysiology of both diabetes and age-related complications. These would include clinical studies aimed at elucidating the benefit of strict glucose control in preventing diabetic complications, as well as experimental investigations of the role of advanced glycosylation in the pathogenesis of such diabetes- and age-related conditions as atherosclerosis, hypertension and renal disease.

EXAMPLE 7

EFFECT OF AMINOGUANIDINE ON URINE AGE LEVELS IN NORMAL AND DIABETIC RATS

Groups of normal and streptozotocin-diabetic rats were left untreated for 11 weeks. Half of the animals in each of the two groups were then started on daily treatment with 70 mg/kg aminoguanidine hydrochloride (AG HCl), by gavage, and the other half of the animals with distilled water by garage. After 10 additional weeks, urines were collected from all animals over a 24 hour period.

Urine samples were centrifuged and the supernatants were diluted eight-fold with 0.3 M potassium phosphate buffer, pH 7.4. Samples of the diluted urines were run in the AGE ELISA assay described above. The results of these measurements are set forth in the Table, below.

TABLE

| Treatment | Urine AGEs: Units excreted per 24 hrs. |
|---|---|
| Normal rats | 5400 ± 1200 |
| Normal rats treated with 70 mg/kg/day AG HCl | 2200 ± 190 |
| Diabetic rats | 9400 ± 340 |
| Diabetic rats treated with 70 mg/kg/day AG HCl | 4100 ± 1200 |

From the above, it was observed that twenty-one weeks of diabetes produced a 1.7-fold increase in urinary AGE excretion over that of normal animals which was normalized by aminoguanidine administration. Aminoguanidine-treated normal rats showed a 60% inhibition of urinary AGE excretion. The above data accordingly confirms the relevance and value of the measurement of urinary AGEs and AGE-peptides to monitor conditions such as diabetes where the turnover of tissue AGEs is a clinically valid long-term determinant, as well as the apparent efficacy of aminoguanidine as a therapeutic agent.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. An antibody reactive with in vivo-formed advanced glycosylation endproducts and having the following characteristics:

A. it reacts with an immunological epitope common to said in vivo-formed advanced glycosylation endproducts;

B. it is cross reactive with advanced glycosylation endproducts formed in vitro; and C. it is not cross reactive with the following model advanced glycosylation endproducts however formed: 2-(2-furoyl)-4(5)-(2-furanyl)-1H-imidazole (FFI), 1alkyl-2-formyl-3,4-diglycosyl pyrrole (AFGP), 5-hydroxymethyl-1-alkylpyrrole-2-carbaldehyde (pyrraline), and pentosidine.

2. The antibody of claim 1 wherein the advanced glycosylation endproducts formed in vitro and reactive with said antibody are selected from the group consisting of AGE-RNAse, AGE-hemoglobin, AGE-albumin, AGE-LDL, AGE-collagen Type IV, AGE-BSA reduced with $NaBH_4$, and mixtures.

3. The antibody of claim 1 prepared by hyperimmunizing a mammal with a foreign protein or the reaction product of a protein incubated with a reducing sugar.

4. The antibody of claim 3 wherein said reaction produce of a protein incubated with a reducing sugar is AGE-RNAse.

5. The antibody of claim 1 wherein said antibody reacts with diabetic tissue and serum that contain elevated levels of advanced glycosylation endproducts.

6. The antibody of claim 5 which reacts with rat aortic collagen from subjects with experimentally-induced diabetes, and with human serum from diabetic subjects.

7. The antibody of claim 1 which is from high titre antiserum.

8. The antibody of claim 7 wherein titre of said antiserum is determined from a serum dilution giving 50% maximum $OD_{405}$ signal using an alkaline phosphatase-conjugated second antibody and p-nitrophenylphosphate as the colorimetric substrate.

9. The antibody of claim 7 wherein said high titre antiserum comprises at least $10^{-5}$ as determined in a noncompetitive ELISA.

10. The antibody of claim 1 wherein said epitope is formed by the incubation of a reducing sugar with a proteinaceous material selected from the group consisting of RNAse, hemoglobin, lysine, collagen Type IV, LDL, BSA and HSA.

11. The antibody of claim 10 wherein the reducing sugar is selected from the group consisting of glucose, glucose-6-phosphate, fructose, and ribose.

12. The antibody of claim 1 wherein said epitope is formed by the incubation of glucose with RNAse.

13. The antibody of claim 1 which is polyclonal.

14. The antibody of claim 1 which is monoclonal.

15. A labeled antibody reactive with in vivo-formed advanced glycosylation endproducts and having the following characteristics:

A. it reacts with an immunological epitope common to said in vivo-formed advanced glycosylation endproducts;

B. it is cross reactive with advanced glycosylation endproducts formed in vitro; and C. it is not cross reactive with the following model advanced glycosylation endproducts however formed: 2-(2-furoyl)-4(5)-(2-furanyl)-1H-imidazole (FFI), 1-alkyl-2-formyl-3,4-diglycosyl pyrrole (AFGP), 5-hydroxymethyl-1-alkylpyrrole-2-carbaldehyde (pyrraline), and pentosidine.

16. The labeled antibody of claim 15 wherein said label is selected from the group consisting of an enzyme, a chemical which fluoresces, and a radioactive element.

17. The labeled antibody of claim 15 which is polyclonal.

18. The labeled antibody of claim 15 which is monoclonal.

19. A composition containing an anti-AGE antibody in combination with a pharmaceutically acceptable carrier;

wherein said anti-AGE antibody is reactive with in vivo-produced advanced glycosylation endproducts and has the following characteristics:

i. it reacts with an immunological epitope common to said in vivo-formed advanced glycosylation endproducts;

ii. it is cross reactive with advanced glycosylation endproducts formed in vitro; and iii. it is not cross reactive with the following advanced glycosylation endproducts however formed: 2-(2-fuwyl)-4(5)-(2-furanyl)-1H-imidazole (FFI); 1-alkyl-2-formyl-3,4-diglycosyl pyrrole (AFGP), 5-hydroxymethyl-1-alkylpyrrole-2-carbaldehyde (pyrraline), and pentosidine.

20. The composition of claim 19 wherein said in vivo-formed advanced glycosylation endproducts are selected from the group consisting of Hb-AGE, AGE-HSA, serum AGE-peptides, urinary AGE-peptides, and combinations thereof.

* * * * *